(12) United States Patent
Miao et al.

(10) Patent No.: US 7,273,851 B2
(45) Date of Patent: Sep. 25, 2007

(54) TRI-PEPTIDE HEPATITIS C SERINE PROTEASE INHIBITORS

(75) Inventors: Zhenwei Miao, San Diego, CA (US); Ying Sun, Waltham, MA (US); Suanne Nakajima, Cambridge, MA (US); Datong Tang, Malden, MA (US); Zhe Wang, Hockessin, DE (US); Yat S. Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 10/849,107

(22) Filed: May 19, 2004

(65) Prior Publication Data

US 2005/0261200 A1    Nov. 24, 2005

Related U.S. Application Data

(60) Provisional application No. 60/560,734, filed on Jun. 5, 2003.

(51) Int. Cl.
*A61K 38/00* (2006.01)

(52) U.S. Cl. ........................................................ 514/18
(58) Field of Classification Search .................. 514/18
See application file for complete search history.

(56) References Cited

U.S. PATENT DOCUMENTS

| | | | |
|---|---|---|---|
| 6,329,379 B1 * | 12/2001 | Llinas-Brunet et al. ..... | 514/256 |
| 6,608,027 B1 | 8/2003 | Tsantrizos et al. | |
| 2002/0037998 A1 | 3/2002 | Llinas-Brunet et al. | |
| 2003/0187018 A1 * | 10/2003 | Llinas-Brunet et al. ..... | 514/312 |
| 2004/0229818 A1 * | 11/2004 | Llinas-Brunet .............. | 514/18 |
| 2005/0049187 A1 * | 3/2005 | Brandenburg et al. ......... | 514/9 |

FOREIGN PATENT DOCUMENTS

| | | |
|---|---|---|
| WO | WO-00/09543 | 2/2000 |
| WO | WO-00/59929 | 10/2000 |
| WO | WO-2003/053349 A3 | 7/2003 |
| WO | WO-2004/072243 A2 | 8/2004 |

OTHER PUBLICATIONS

Ingallinella et al, Potent peptide inhibitors of humas hepatitis C virus NS3 protease are obtained by optimizing the cleavage products, Biochemistry (1998) vol. 37, 8906-8914.*
March, "Advanced Organinc Chemistry," 3rd Edition, p. 312.*
Llinas-Brunet et al., Peptide-Based Inhibitors of the Hepatitis C Virus Serine Protease, Biorg. Med. Chem., Letters 8 (1998), 1713-1718.
A. Spatola, "Peptide Backbone Modifications: A Structure-Activity Analysis of Peptides Containing Amide Bond Surrogates, Conformational Constraints, and Rela," Department of Chemistry, University of Louisville, Louisville Kentucky, pp. 267-357, XP 002032461.

* cited by examiner

*Primary Examiner*—Ceceilia J. Tsang
*Assistant Examiner*—Thomas S. Heard
(74) *Attorney, Agent, or Firm*—Edwards Angell Palmer & Dodge LLC; Jeffrey Hsi

(57) ABSTRACT

The present invention relates to compounds of Formula I, or a pharmaceutically acceptable salt, ester, or prodrug, thereof:

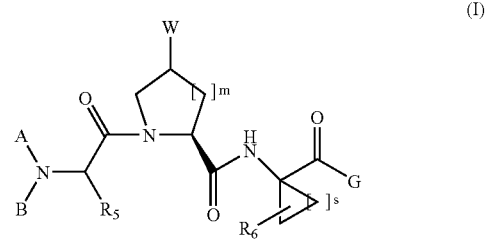

(I)

which inhibit serine protease activity, particularly the activity of hepatitis c virus (HCV) NS3-NS4A protease. Consequently, the compounds of the present invention interfere with the life cycle of the hepatitis c virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

18 Claims, No Drawings

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 1
gctgcggcct gtcgagct                                          18

<210> SEQ ID NO 2
<211> LENGTH: 19
<212> TYPE: DNA

```
<213> ORGANISM: Artificial Sequence
<220> FEATURE:
<223> OTHER INFORMATION: Description of Artificial Sequence: Primer

<400> SEQUENCE: 2
caaggtcgtc tccgcatac                                                19

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Probe
<220> FEATURE:
<223> OTHER INFORMATION: see specification as filed for preferred
      embodiments

<400> SEQUENCE: 3
cgaagctcca ggactgcacg atgct                                         25

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for preferred
      embodiments
<220> FEATURE:
<221> NAME/KEY: MOD_RES
<222> LOCATION: (6)
<223> OTHER INFORMATION: Abu

<400> SEQUENCE: 4

Asp Glu Asp Glu Glu Xaa Ala Ser Lys
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for preferred
      embodiments

<400> SEQUENCE: 5

Asp Glu Met Glu Glu Cys
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Dif
<220> FEATURE:
```

```
<221> NAME/KEY: MOD_RES
<222> LOCATION: (4)
<223> OTHER INFORMATION: Cha
<220> FEATURE:
<223> OTHER INFORMATION: see specification as filed for preferred
      embodiments

<400> SEQUENCE: 6

Asp Glu Xaa Xaa Cys
 1               5
```

TRI-PEPTIDE HEPATITIS C SERINE PROTEASE INHIBITORS

CROSS-REFERENCE TO RELATED APPLICATIONS

This application claims benefit to U.S. provisional application Ser. No. 60/560,734 (conversion of U.S. Ser. No. 10/454,997) filed Jun. 5, 2003, the entirety of which is herein incorporated by reference.

TECHNICAL FIELD

The present invention relates to novel tripeptides having activity against hepatitis C virus (HCV) and useful in the treatment of HCV infections. More particularly, the invention relates to tripeptide compounds, compositions containing such compounds and methods for using the same, as well as processes for making such compounds.

BACKGROUND OF THE INVENTION

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantations in the western world.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

Only two approved therapies for HCV infection are currently available. The original treatment regimen generally involves a 3–12 month course of intravenous interferon-α (IFN-α), while a new approved second-generation treatment involves co-treatment with IFN-α and the general antiviral nucleoside mimics like ribavirin. Both of these treatments suffer from interferon related side effects as well as low efficacy against HCV infections. There exists a need for the development of effective antiviral agents for treatment of HCV infection due to the poor tolerability and disappointing efficacy of existing therapies.

In a patient population where the majority of individuals are chronically infected and asymptomatic and the prognoses are unknown, an effective drug must possess significantly fewer side effects than the currently available treatments. The hepatitis C non-structural protein-3 (NS3) is a proteolytic enzyme required for processing of the viral polyprotein and consequently viral replication. Despite the huge number of viral variants associated with HCV infection, the active site of the NS3 protease remains highly conserved thus making its inhibition an attractive mode of intervention. Recent success in the treatment of HIV with protease inhibitors supports the concept that the inhibition of NS3 is a key target in the battle against HCV.

HCV is a flaviridae type RNA virus. The HCV genome is enveloped and contains a single strand RNA molecule composed of circa 9600 base pairs. It encodes a polypeptide comprised of approximately 3010 amino acids.

The HCV polyprotein is processed by viral and host peptidase into 10 discreet peptides which serve a variety of functions. There are three structural proteins, C, E1 and E2. The P7 protein is of unknown function and is comprised of a highly variable sequence. There are six non-structural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease.

The NS3.4A protease is responsible for cleaving four sites on the viral polyprotein. The NS3-NS4A cleavage is autocatalytic, occurring in cis. The remaining three hydrolyses, NS4A-NS4B, NS4B-NS5A and NS5A-NS5B all occur in trans. NS3 is a serine protease which is structurally classified as a chymotrypsin-like protease. While the NS serine protease possesses proteolytic activity by itself, the HCV protease enzyme is not an efficient enzyme in terms of catalyzing polyprotein cleavage. It has been shown that a central hydrophobic region of the NS4A protein is required for this enhancement. The complex formation of the NS3 protein with NS4A seems necessary to the processing events, enhancing the proteolytic efficacy at all of the sites.

A general strategy for the development of antiviral agents is to inactivate virally encoded enzymes, including NS3, that are essential for the replication of the virus. Current efforts directed toward the discovery of NS3 protease inhibitors were reviewed by S. Tan, A. Pause, Y. Shi, N. Sonenberg, Hepatitis C Therapeutics: Current Status and Emerging Strategies, *Nature Rev. Drug Discov.*, 1, 867–881 (2002). More relevant patent disclosures describing the synthesis of HCV protease inhibitors are: US 2003/0008828; WO 00/59929 (2000); WO 03/006490 (2003); WO 99/07733 (1999); WO 00/09543 (2000); WO 99/50230 (1999); U.S. Pat. No. 5,861,297 (1999).

SUMMARY OF THE INVENTION

The present invention relates to novel tripeptide compounds and methods of treating a hepatitis C infection in a subject in need of such therapy with said tripeptide compounds. The present invention further relates to pharmaceutical compositions comprising the compounds of the present invention, or pharmaceutically acceptable salts, esters, or prodrugs thereof, alone or in combination with a pharmaceutically acceptable carrier or excipient.

In one embodiment of the present invention there are disclosed compounds represented by Formula I, or pharmaceutically acceptable salts, esters, or prodrugs thereof:

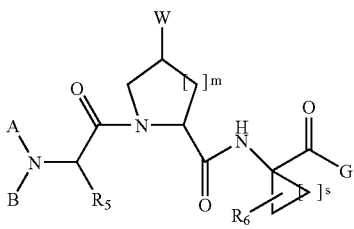

(I)

A and B are independently selected from $R_1$, —C(O)$R_1$, —C(O)O$R_1$, —C(O)N$R_3R_4$, —C(S)N$R_3R_4$, or —S(O)$_nR_1$;

G is selected from —$R_1$, —O$R_1$, —C(O)$R_1$, —C(O)O$R_1$, —C(O)N$R_3R_4$, —N$R_3R_4$, or —N($R_3$)S(O)$_nR_1$;

W is selected from a suitable leaving group, a substituted or unsubstituted heterocyclic, or a substituted or unsubstituted heteroaromatic;

Each $R_1$ is independently selected from: hydrogen, deuterium, acyl, silane, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group;

Each of $R_3$ and $R_4$ is independently selected from: hydrogen, acyl, ester, optionally substituted amino acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, a substituted or unsubstituted heterocyclic group; or can be taken together with the nitrogen atom to which they are attached to form a substituted or unsubstituted heterocyclic or heteroaromatic ring;

Each of $R_5$ and $R_6$ are independently selected from: hydrogen, deuterium, acyl, silane, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group alkoxy, alkyl amine, hydroxy, hydroxylamine, carboxy, ester, amine;

m is 0, 1, or 2;
n is 0, 1, or 2; and
s is 1, 2, 3 or 4.

DETAILED DESCRIPTION OF THE INVENTION

A first embodiment of the invention is a compound represented by Formula I as described above, or a pharmaceutically acceptable salt, ester or prodrug thereof, in combination with a pharmaceutically acceptable carrier or excipient.

Representative subgenera of the invention include, but are not limited to:

A compound of formula I, wherein W is OMs (—O-Mesylate).

A compound of formula I, wherein m is equal to 1 and s is equal to 1.

A compound of formula I, wherein $R_5$ is t-butyl and $R_6$ is vinyl.

A compound of formula I, wherein W is selected from: substituted or unsubstituted triazolyl, substituted or unsubstituted tetrazolyl, substituted or unsubstituted pyridazinonyl, substituted or unsubstituted pyrrolyl, substituted or unsubstituted pyrrolidinyl, substituted or unsubstituted imidazolyl, substituted or unsubstituted oxazolidinyl, substituted or unsubstituted oxazolinyl, substituted or unsubstituted oxazolyl, substituted or unsubstituted piperidinyl, substituted or unsubstituted pyridinyl, substituted or unsubstituted pyridazinyl, substituted or unsubstituted pyrimidinyl, substituted or unsubstituted triazinyl, substituted or unsubstituted aziridinyl, substituted or unsubstituted indolyl, substituted or unsubstituted benzimidazolyl, substituted or unsubstituted aziridinyl, substituted or unsubstituted azetidinyl, substituted or unsubstituted 4,5-dihydro-1H-pyrazolyl, substituted or unsubstituted pyrazolidinyl, substituted or unsubstituted imidazolidinyl, substituted or unsubstituted imidazolidinyl, substituted or unsubstituted pyrrolidinyl, substituted or unsubstituted pyrrolidinyl, substituted or unsubstituted pipiridinyl, substituted or unsubstituted piperizinyl, substituted or unsubstituted morphoninyl, or substituted or unsubstituted thiomorpholinyl.

A compound of formula I, wherein:
W is selected from

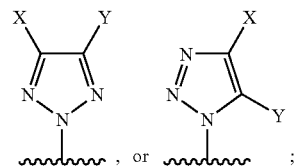

X and Y are independently selected from: H, halogen, $C_1-C_6$ alkyl, $C_3-C_{12}$ cycloalkyl, —$CH_2$-alkylamino, —$CH_2$-dialkylamino, —$CH_2$-arylamino, —$CH_2$-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, or substituted heterocycloalkyl; and in the alternative, X and Y taken together with the carbon atoms occupying the 4 and 5 positions of the triazole ring, to which X and Y are attached, form a cyclic moiety selected from aryl, substituted aryl, heteroaryl, or substituted heteroaryl.

A compound of formula I, wherein:
W is selected from the group consisting of:

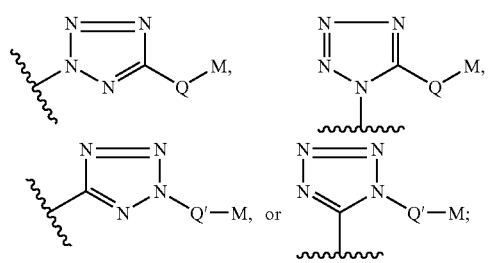

Q is selected from the group consisting of: absent, —$CH_2$—, —O—, —NH—, —N($R_1$)—, —S—, —S(O)$_2$—, and —(C=O)—;

Q' is selected from the group consisting of: absent, —$CH_2$—, and —NH—; Y is selected from the group consisting of: H, $C_1-C_6$ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; and M is independently selected from —$R_1$.

A compound of formula I, wherein:

W is

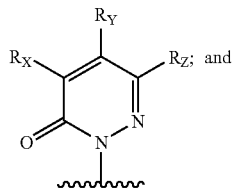

$R_X$, $R_Y$, and $R_Z$ are independently selected from the group consisting of H, $N_3$, halogen, $C_1$–$C_6$ alkyl, $C_3$–$C_{12}$ cycloalkyl, alkylamino, dialkylamino, $C_1$–$C_6$ alkynyl, substituted alkynyl, aryl, substituted aryl, —S-aryl, —S-substituted aryl, —O-aryl, —O-substituted aryl, NH-aryl, NH-substituted aryl, diarylamino, diheteroarylamino, arylalkyl, substituted arylalkyl, heteroaryl, substituted heteroaryl, —S-heteroaryl, —S-substituted heteroaryl, —O-heteroaryl, —O-substituted heteroaryl, —NH-heteroaryl, —NH-substituted heteroaryl, heteroarylalkyl, substituted heteroarylalkyl, heterocycloalkyl, and substituted heterocycloalkyl; or, in the alternative, $R_X$ and $R_Y$ or $R_Y$ and $R_Z$ taken together with the carbon atoms to which they are attached form an aryl, substituted aryl, heteroaryl, or substituted heteroaryl cyclic moiety.

According to an alternate embodiment, the pharmaceutical compositions of the present invention may further contain other anti-HCV agents. Examples of anti-HCV agents include, but are not limited to, α-interferon, β-interferon, ribavirin, and amantadine.

According to an additional alternate embodiment, the pharmaceutical compositions of the present invention may further contain other HCV protease inhibitors.

According to yet another alternate embodiment, the pharmaceutical compositions of the present invention may further comprise inhibitor(s) of other targets in the HCV life cycle, including, but not limited to, helicase, polymerase, metalloprotease, and internal ribosome entry site (IRES).

According to a further embodiment, the present invention includes methods of treating hepatitis C infections in a subject in need of such treatment by administering to said subject a therapeutically effective amount of the pharmaceutical compositions of the present invention. In addition the present invention contemplates the use of said the compounds of the instant invention or said pharmaceutical compositions for pre-treatment of invasive devices to be inserted into a subject or to treat biological samples, such as blood, prior to administration to a subject. Moreover, the pharmaceutical compositions of the present invention can be used to inhibit HCV replication and to lessen the risk of or the severity of HCV infection.

Another embodiment of the invention provides methods of treating materials that may have come in contact with a virus characterized by a virally encoded serine protease necessary for its life cycle. This method comprises the step of contacting said material with a compound of the present invention. Such materials include, but are not limited to, surgical instruments and garments; blood collection apparatuses and materials and invasive devices, such as shunts, stents, etc.

In yet another embodiment, the compounds of the present invention may be used as laboratory tools to aid in the isolation of a virally encoded serine protease. This method comprises the steps of providing a compound of this invention attached to a solid support; contacting said solid support with a sample containing a viral serine protease under conditions that cause said protease to bind to said solid support; and eluting said serine protease from said solid support. Preferably, the viral serine protease isolated by this method is HCV NS3-NS4A protease.

In addition, the present invention contemplates processes by which to make any compound delineated herein by any synthetic method disclosed herein.

Definitions

Listed below are definitions of various terms used to describe this invention. These definitions apply to the terms as they are used throughout this specification and claims, unless otherwise limited in specific instances, either individually or as part of a larger group.

An "aliphatic group" is non-aromatic moiety that may contain any combination of carbon atoms, hydrogen atoms, halogen atoms, oxygen, nitrogen, sulfur or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

Suitable aliphatic or aromatic substituents include, but are not limited to, the following suitable substituents: —F, —Cl, —Br, —I, —OH, protected hydroxy, aliphatic ethers, aromatic ethers, oxo, —$NO_2$, —CN, —CHO, imine, oxime, —$C_1$–$C_{12}$-alkyl optionally substituted with halogen (such as perhaloalkyls), —$C_2$–$C_{12}$-alkenyl optionally substituted with halogen, —$C_2$–$C_{12}$-alkynyl optionally substituted with halogen, —$NH_2$, protected amino, —NH—$C_1$–$C_{12}$-alkyl, —NH—$C_2$–$C_{12}$-alkenyl, —NH—$C_2$–$C_{12}$-alkenyl, —NH—$C_3$–$C_{12}$-cycloalkyl, —NH-aryl, —NH-heteroaryl, —NH-heterocycloalkyl, -dialkylamino, -diarylamino, -diheteroarylamino, —O—$C_1$–$C_{12}$-alkyl, —O—$C_2$–$C_{12}$-alkenyl, —O—$C_2$–$C_{12}$-alkynyl, —O—$C_3$–$C_{12}$-cycloalkyl, —O-aryl, —O-heteroaryl, —O-heterocycloalkyl, —C(O)—$C_1$–$C_{12}$-alkyl, —C(O)—$C_2$–$C_{12}$-alkenyl, —C(O)—$C_2$–$C_{12}$-alkynyl, —C(O)—$C_3$–$C_{12}$-cycloalkyl, —C(O)-aryl, C(O)-heteroaryl, —C(O)-heterocycloalkyl, —$CONH_2$, —CONH—$C_1$–$C_{12}$-alkyl, —CONH—$C_2$–$C_{12}$-alkenyl, —CONH—$C_2$–$C_{12}$-alkynyl, —CONH—$C_3$–$C_{12}$-cycloalkyl, —CONH-aryl, —CONH-heteroaryl, —CONH-heterocycloalkyl, —$CO_2$—$C_1$–$C_{12}$-alkyl, —$CO_2$—$C_2$–$C_{12}$-alkenyl, —$CO_2$—$C_2$–$C_{12}$-alkynyl, —$CO_2$—$C_3$–$C_{12}$-cycloalkyl, —$CO_2$-aryl, —$CO_2$-heteroaryl, —$CO_2$-heterocycloalkyl, —$CO_2$—$C_1$–$C_{12}$-alkyl, —$OCO_2$—$C_2$–$C_{12}$-alkenyl, —$OCO_2$—$C_2$–$C_{12}$-alkynyl, —$OCO_2$—$C_3$–$C_{12}$-cycloalkyl, —$OCO_2$-aryl, —$OCO_2$-heteroaryl, —$OCO_2$-heterocycloalkyl, —$OCONH_2$, —OCONH—$C_1$–$C_{12}$-alkyl, —OCONH—$C_2$–$C_{12}$-alkenyl, —OCONH—$C_2$–$C_{12}$-alkynyl, —OCONH—$C_3$–$C_{12}$-cycloalkyl, —OCONH-aryl, —OCONH-heteroaryl, —OCONH-heterocycloalkyl, —NHC(O)—$C_1$–$C_{12}$-alkyl, —NHC(O)—$C_2$–$C_{12}$-alkenyl, —NHC(O)—$C_2$–$C_{12}$-alkynyl, —NHC(O)—$C_3$–$C_{12}$-cycloalkyl, —NHC(O)-aryl, —NHC(O)- heteroaryl, —NHC(O)-heterocycloalkyl, —NHCO$_2$—C$_1$–C$_{12}$-alkyl, —NHCO$_2$—C$_2$–C$_{12}$-alkenyl, —NHCO$_2$—C$_2$–C$_{12}$-alkynyl, —NHCO$_2$—C$_3$–C$_{12}$-cycloalkyl, —NHCO$_2$-aryl, —NHCO$_2$-heteroaryl, —NHCO$_2$-heterocloalkyl, —NHC(O)NH$_2$, —NHC(O)NH—C$_1$–C$_{12}$-alkyl, —NHC(O)NH—C$_2$–C$_{12}$alkenyl, —NHC(O)NH—C$_2$–C$_{12}$-alkynyl, —NHC(O)NH—C$_3$–C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$–C$_{12}$-alkyl, —NHC(S)NH—C$_2$–C$_{12}$-alkenyl, —NHC(S)NH—C$_2$–C$_{12}$-alkynyl, —NHC(S)NH—C$_3$–C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$–C$_{12}$-alkyl, —NHC(NH)NH—C$_2$–C$_{12}$-alkenyl, —NHC(NH)NH—C$_2$–C$_{12}$-alkynyl, —NHC(NH)NH—C$_3$–C$_{12}$-cycloalkyl, —NHC(NH)NH-aryl, —NHC(NH)NH-heteroaryl, —NHC(NH)NH-heterocycloalkyl, —NHC(NH)—C$_1$–C$_{12}$-alkyl, —NHC(NH)—C$_2$–C$_{12}$-alkenyl, —NHC(NH)—C$_2$–C$_{12}$-alkynyl, —NHC(NH)—C$_3$–C$_{12}$-cycloalkyl, —NHC(NH)-aryl, —NHC(NH)-heteroaryl, —NHC(NH)-heterocycloalkyl, —(NH)NH—C$_1$–C$_{12}$-alkyl, —C(NH)NH—C$_2$–C$_{12}$-alkenyl, —(NH)NH—C$_2$–C$_{12}$-alkynyl, —C(NH)NH—C$_3$–C$_{12}$-cycloalkyl, —C(NH)NH-aryl, —C(NH)NH-heteroaryl, —C(NH)NH-heterocycloalkyl, —S(O)—C$_1$–C$_{12}$-alkyl, —S(O)—C$_2$–C$_{12}$-alkenyl, —S(O)—C$_2$–C$_{12}$-alkynyl, —S(O)—C$_3$–C$_{12}$-cycloalkyl, —S(O)-aryl, —S(O)-heteroaryl, —S(O)-heterocycloalkyl, —SO$_2$NH$_2$, —SO$_2$NH—C$_1$–C$_{12}$-alkyl, —SO$_2$NH—C$_2$–C$_{12}$-alkenyl, —SO$_2$NH—C$_2$–C$_{12}$-alkynyl, —SO$_2$NH—C$_3$–C$_{12}$-cycloalkyl, —SO$_2$NH-aryl, —SO$_2$NH-heteroaryl, —SO$_2$NH-heterocycloalkyl, —NHSO$_2$—C$_1$–C$_{12}$-alkyl, —NHSO$_2$—C$_2$–C$_{12}$-alkenyl, —NHSO$_2$—C$_2$–C$_{12}$-alkynyl, —NHSO$_2$—C$_3$–C$_{12}$-cycloalkyl, —NHSO$_2$-aryl, —NHSO$_2$-heteroaryl, —NHSO$_2$-heterocycloalkyl; —CH$_2$NH$_2$, —CH$_2$SO$_2$CH$_3$, -aryl, -arylalkyl, -heteroaryl, -heteroarylalkyl, -heterocycloalkyl, —C$_3$–C$_{12}$-cycloalkyl, polyalkoxyalkyl, polyalkoxy, methoxymethoxy, methoxyethoxy, —SH, —S—C$_1$–C$_{12}$-alkyl, —S—C$_2$–C$_{12}$-alkenyl, —S—C$_2$–C$_{12}$-alkynyl, —S—C$_3$–C$_{12}$-cycloalkyl, —S-aryl, —S-heteroaryl, —S-heterocycloalkyl, or methylthiomethyl. It is understood that the aryls, heteroaryls, alkyls, and heterocylics and the like can be further substituted.

The terms "C$_2$–C$_{12}$ alkenyl" or "C$_2$–C$_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, alkadienes and the like.

The term "substituted alkenyl," as used herein, refers to a "C$_2$–C$_{12}$ alkenyl" or "C$_2$–C$_6$ alkenyl" group as previously defined, substituted by one, two, three or more aliphatic substituents.

The terms "C$_2$–C$_{12}$ alkynyl" or "C$_2$–C$_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "C$_2$–C$_{12}$ alkynyl" or "C$_2$–C$_6$ alkynyl" group as previously defined, substituted by one, two, three or more aliphatic substituents.

The term "C$_1$–C$_6$ alkoxy," as used herein, refers to a C$_1$–C$_6$ alkyl group, as previously defined, attached to the parent molecular moiety through an oxygen atom. Examples of C$_1$–C$_6$-alkoxy include, but are not limited to, methoxy, ethoxy, propoxy, isopropoxy, n-butoxy, sec-butoxy, tert-butoxy, n-pentoxy, neopentoxy and n-hexoxy.

The terms "halo" and "halogen," as used herein, refer to an atom selected from fluorine, chlorine, bromine and iodine.

The terms "aryl" or "aromatic" as used herein, refer to a mono- or bicyclic carbocyclic ring system having one or two aromatic rings including, but not limited to, phenyl, naphthyl, tetrahydronaphthyl, indanyl, and the like.

The terms "substituted aryl" or "substituted aromatic," as used herein, refer to an aryl or aromatic group substituted by one, two, three or more aromatic substituents.

The term "arylalkyl," as used herein, refers to an aryl group attached to the parent compound via a C$_1$–C$_3$ alkyl or C$_1$–C$_6$ alkyl residue. Examples include, but are not limited to, benzyl, phenethyl and the like.

The term "substituted arylalkyl," as used herein, refers to an arylalkyl group, as previously defined, substituted by one, two, three or more aromatic substituents.

The terms "heteroaryl" or "heteroaromatic," as used herein, refer to a mono-, bi-, or tri-cyclic aromatic radical or ring having from five to ten ring atoms of which at least one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The heteroaromatic ring may be bonded to the chemical structure through a carbon or hetero atom.

The terms "substituted heteroaryl" or "substituted heteroaromatic," as used herein, refer to a heteroaryl or heteroaromatic group, substituted by one, two, three, or more aromatic substituents.

The term "C$_3$–C$_{12}$-cycloalkyl" or "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl.

The term "C$_3$–C$_{12}$-cycloalkyl" or "substituted alicyclic," as used herein, refers to an alicyclic group substituted by one, two, three or more aliphatic substituents.

The term "heterocyclic" or "heterocycloalkyl," as used herein, refers to a non-aromatic ring, comprising three or more ring atoms, or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl.

The term "substituted heterocycloalkyl" or "substituted heterocyclic," as used herein, refers to a heterocyclic group, as previously defined, substituted by one, two, three or more aliphatic substituents.

The term "heteroarylalkyl," as used herein, to a heteroaryl group attached to the parent compound via a $C_1$–$C_3$ alkyl or $C_1$–$C_6$ alkyl residue. Examples include, but are not limited to, pyridinylmethyl, pyrimidinylethyl and the like.

The term "substituted heteroarylalkyl," as used herein, refers to a heteroarylalkyl group, as previously defined, substituted by independent replacement of one, two, or three or more aromatic substituents.

The term "heterocycle," as used herein, refers to a heteroaromatic or a heterocyclic group as previously defined.

The term "substituted heterocycle," as used herein, refers to a heterocycle group, as previously defined, substituted by independent replacement of one, two, or three or more aromatic substituents.

The term "alkylamino" refers to a group having the structure —NH($C_1$–$C_{12}$ alkyl).

The term "dialkylamino" refers to a group having the structure —N($C_1$–$C_{12}$ alkyl)($C_1$–$C_{12}$ alkyl) and cyclic amines. Examples of dialkylamino are, but not limited to, dimethylamino, diethylamino, methylethylamino, piperidino, morpholino and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH($C_1$–$C_{12}$ alkyl) or —C(O)N($C_1$–$C_{12}$ alkyl)($C_1$–$C_{12}$ alkyl), —C(O)NH$_2$, NHC(O)($C_1$–$C_{12}$ alkyl), N($C_1$–$C_{12}$ alkyl)C(O)($C_1$–$C_{12}$ alkyl) and the like.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis*, 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "protected hydroxy," as used herein, refers to a hydroxy group protected with a hydroxy protecting group, as defined above, including benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl(Bz or —C(O)C$_6$H$_5$), and trimethylsilyl (TMS or —Si(CH$_3$)$_3$).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis*, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. 1, in the *Techniques of Chemistry Series*, John Wiley & Sons, NY, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations,* VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995).

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1–19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991); Bundgaard, et al., Journal of Drug Deliver Reviews, 8:1–38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The term "subject" as used herein refers to an animal. Preferably the animal is a mammal. More preferably the mammal is a human. A subject also refers to, for example, dogs, cats, horses, cows, pigs, guinea pigs, fish, birds and the like.

The term "biological sample(s)," as used herein, means a substance of biological origin intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof; or stem cells.

This invention also encompasses pharmaceutical compositions and methods of reducing the hepatitis C viral load in a subject through administering, pharmaceutically acceptable prodrugs of compounds of the present invention. For example, compounds having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula I. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including, but not limited to, ether, amine and carboxylic acid functionalities.

Suitable concentrations of reactants are 0.01M to 10M, typically 0.1M to 1M. Suitable temperatures include −10° C. to 250° C., typically −78° C. to 150° C., more typically −78° C. to 100° C., still more typically 0° C. to 100° C. Reaction vessels are preferably made of any material which does not substantial interfere with the reaction. Examples include glass, plastic, and metal. The pressure of the reaction can advantageously be operated at atmospheric pressure. The atmospheres includes, for example, air, for oxygen and water insensitive reactions, or nitrogen or argon, for oxygen or water sensitive reactions.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. In addition to inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and I) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Antiviral Activity

According to the methods of treatment of the present invention, viral infections are treated or prevented in a subject, such as a human or lower mammal, by administering to the subject therapeutically effective amount of a compound of the present invention, in such amounts and for such time as is necessary to achieve the desired result. An additional method of the present invention is the treatment of biological samples with a therapeutically effective amount of a compound of composition of the present invention in such amounts and for such time as is necessary to achieve the desired result.

By a "therapeutically effective amount" of a compound of the invention is meant a sufficient amount of the compound to treat or prevent hepatitis C infections in a subject, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

Another embodiment of the present invention is a method of treating a biological sample by contacting said biological sample with a therapeutically effective amount of a compound or pharmaceutical composition of the present invention.

In a further aspect of the invention, the therapeutic method of the invention further comprises a co-therapeutic treatment regimen comprising administering a therapeutically effective amount of an anti-hepatitis C virus agent or inhibitor of the hepatitis C virus life cycle, in combination with a therapeutically effective amount of the compositions of the invention to treat disease in a patient. As used herein a "co-therapeutic treatment regimen" means a treatment regimen wherein two drugs are administered simultaneously, in either separate or combined formulations, or sequentially at different times separated by minutes, hours or days, but in some way act together to provide the desired therapeutic response. Any known anti-hepatitis C virus agent or HCV life cycle inhibitor suitable for the treating the particular disease and the particular patient may be used in accordance with the invention. Such suitable anti-hepatitis C virus agents include but are not limited to α-interferon, β-interferon, ribavarin, and adamantine. Suitable HCV life cycle inhibitors include helicase, polymerase, metalloprotease, and IRES Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific therapeutically effective dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily therapeutically effective dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods delineated herein contemplate administration of a therapeutically effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Assays to Determine HCV Inhibition

NS3/NS4a Protease Enzyme Assay

HCV protease activity and inhibition is assayed using an internally quenched fluorogenic substrate. A DABCYL and an EDANS group are attached to opposite ends of a short peptide. Quenching of the EDANS fluorescence by the DABCYL group is relieved upon proteolytic cleavage. Fluo rescence was measured with a Molecular Devices Fluoromax (or equivalent) using an excitation wavelength of 355 nm and an emission wavelength of 485 nm.

The assay is run in Corning white half-area 96-well plates (VWR 29444-312) with full-length NS3 HCV protease 1b tethered with NS4A cofactor (final enzyme concentration 1 to 15 nM). The assay buffer is complemented with 10 μM NS4A cofactor Pep 4A (Anaspec 25336 or in-house, MW 1424.8). RET S1 (Ac-Asp-Glu-Asp(EDANS)-Glu-Glu-Abu-Ala-Ser-Lys-(DABCYL)-$NH_2$ (SEQ ID NO: 4), AnaSpec 22991, MW 1548.6) is used as the fluorogenic peptide substrate. The assay buffer contained 50 mM Hepes at pH 7.5, 30 mM NaCl and 10 mM BME. The enzyme reaction is followed over a 30 minutes time course at room temperature in the absence and presence of inhibitors.

The peptide inhibitors HCV Inh 1 (Anaspec 25345, MW 796.8) Ac-Asp-Glu-Met-Glu-Glu-Cys-OH (SEQ ID NO: 5) and HCV Inh 2 (Anaspec 25346, MW 913.1) Ac-Asp-Glu-Dif-Cha-Cys-OH (SEQ ID NO: 6), were used as reference compounds.

IC50 values were calculated using XLFit in ActivityBase (IDBS) using equation 205: $y=A+((B-A)/(1+((C/x)^D)))$.

Cell-Based Replicon Assay

Quantification of HCV Replicon RNA in Cell Lines (HCV Cell Based Assay)

Cell lines, including Huh-11-7 or Huh 9-13, harboring HCV replicons (Lohmann, et al Science 285:110–113, 1999) are seeded at $5\times10^3$ cells/well in 96 well plates and fed media containing DMEM (high glucose), 10% fetal calf serum, penicillin-streptomycin and non-essential amino acids. Cells are incubated in a 5% $CO_2$ incubator at 37° C. At the end of the incubation period, total RNA is extracted and purified from cells using Qiagen Rneasy 96 Kit (Catalog No. 74182). To amplify the HCV RNA so that sufficient material can be detected by an HCV specific probe (below), primers specific for HCV (below) mediate both the reverse transcription (RT) of the HCV RNA and the amplification of the cDNA by polymerase chain reaction (PCR) using the TaqMan One-Step RT-PCR Master Mix Kit (Applied Biosystems catalog no. 4309169). The nucleotide sequences of the RT-PCR primers, which are located in the NS5B region of the HCV genome, are the following:

standard curve of HCV RNA standards with known copy number (ABI User Bulletin #2 Dec. 11, 1997).

The RT-PCR product was detected using the following labeled probe:

5'FAM-CGAAGCTCCAGGACTGCACGATGCT-TAMRA SEQ ID No: 3

FAM=Fluorescence reporter dye.

TAMRA:=Quencher dye.

The RT reaction is performed at 48° C. for 30 minutes followed by PCR. Thermal cycler parameters used for the PCR reaction on the ABI Prism 7700 Sequence Detection System were: one cycle at 95° C., 10 minutes followed by 35 cycles each of which included one incubation at 95° C. for 15 seconds and a second incubation for 60° C. for 1 minute.

To normalize the data to an internal control molecule within the cellular RNA, we perform RT-PCR on the cellular messenger RNA glyceraldehydes-3-phosphate dehydrogenase (GAPDH). The GAPDH copy number is very stable in the cell lines used. GAPDH RT-PCR is performed on the same exact RNA sample from which the HCV copy number is determined. The GAPDH primers and probes, as well as the standards with which to determine copy number, is contained in the ABI Pre-Developed TaqMan Assay Kit (catalog no. 4310884E). The ratio of HCV/GAPDH RNA is used to calculate the activity of compounds evaluated for inhibition of HCV RNA replication.

Activity of Compounds as Inhibitors of HCV Replication (Cell Based Assay) in Replicon Containing Huh-7 Cell Lines The effect of a specific anti-viral compound on HCV replicon RNA levels in Huh-11-7 or 9–13 cells, cells was determined by comparing the amount of HCV RNA normalized to GAPDH (e.g. the ratio of HCV/GAPDH) in the cells exposed to compound versus cells exposed to the 0% inhibition and the 100% inhibition controls. Specifically, cells were seeded at $5\times10^3$ cells/well in a 96 well plate and were incubated either with: 1) media containing 1% DMSO (0% inhibition control), 2) 100 international units, IU/ml Interferon-alpha 2b in media/1% DMSO or 3) media/1% DMSO containing a fixed concentration of compound. 96 well plates as described above were then incubated at 37° C.

```
HCV Forward primer "RBNS5bfor": 5'GCTGCGGCCTGTCGAGCT  SEQ ID No: 1

HCV Reverse primer "RBNS5Brev": 5'CAAGGTCGTCTCCGCATAC SEQ ID No. 2
```

Detection of the RT-PCR product was accomplished using the Applied Biosystem (ABI) Prism 7700 Sequence Detection System (SDS) that detects the fluorescence that is emitted when the probe, which is labeled with a fluorescence reporter dye and a quencher dye, is processed during the PCR reaction. The increase in the amount of fluorescence is measured during each cycle of PCR and reflects the increasing amount of RT-PCR product. Specifically, quantification is based on the threshold cycle, where the amplification plot crosses a defined fluorescence threshold. Comparison of the threshold cycles of the sample with a known standard provides a highly sensitive measure of relative template concentration in different samples (ABI User Bulletin #2 Dec. 11, 1997). The data is analyzed using the ABI SDS program version 1.7. The relative template concentration can be converted to RNA copy numbers by employing a for 3 days (primary screening assay) or 4 days (IC50 determination). Percent inhibition was defined as:

% Inhibition=$[100-((S-C2)/C1-C2))]\times100$, where a) S=the ratio of HCV RNA copy number/GAPDH RNA copy number in the sample;

b) C1=the ratio of HCV RNA copy number/GAPDH RNA copy number in the 0% inhibition control (media/1% DMSO); and c) C2=the ratio of HCV RNA copy number/GAPDH RNA copy number in the 100% inhibition control (100 IU/ml Interferon-alpha 2b).

The dose-response curve of the inhibitor was generated by adding compound in serial, three-fold dilutions over three logs to wells starting with the highest concentration of a specific compound at 10 uM and ending with the lowest concentration of 0.01 uM. Further dilution series (1 uM to 0.001 uM for example) was performed if the IC50 value was not in the linear range of the curve. IC50 was determined based on the IDBS Activity Base program using Microsoft Excel "XL Fit" in which A=100% inhibition value (100 IU/ml Interferon-alpha 2b), B=0% inhibition control value (media/1% DMSO) and C=midpoint of the curve as defined as C=(B−A/2)+A. A, B and C values are expressed as the ratio of HCV RNA/GAPDH RNA as determined for each sample in each well of a 96 well plate as described above. For each plate the average of 4 wells were used to define the 100% and 0% inhibition values.

Unless otherwise defined, all technical and scientific terms used herein are accorded the meaning commonly known to one of ordinary skill in the art. All publications, patents, published patent applications, and other references mentioned herein are hereby incorporated by reference in their entirety Abbreviations Abbreviations which have been used in the descriptions of the scheme and the examples that follow are:

BOP is benzotriazol-1-yloxy-tris(dimethylamino)phosphonium hexafluorophosphate;
DCM for dichloromethane;
DIAD for diisopropyl azodicarboxylate;
DIEA for diisopropyl ethylamine;
DMAP for N,N-dimethylaminopyridine;
DME for ethylene glycol dimethyl ether;
DMF for N,N-dimethyl formamide;
EtOAc for ethyl acetate;
HATU for O(7-Azabenzotriazole-1-yl)-N,N,N',N'-tetramethyluronium hexafluorophosphate;
HMBA is 4-Hydroxymethylbenzoic acid AM resin;
KHMDS is potassium bis(trimethylsilyl)amide;
Ms for mesyl;
PyBrOP for Bromo-tri-pyrolidino-phosphonium hexafluorophosphate;
Ph for phenyl;
RT for room temperature;
TEA for triethyl amine;
TFA for trifluoroacetic acid;
THF for tetrahydrofuran;
TMS for trimethyl silyl;
TPP or PPh$_3$ for triphenylphosphine; and
tBOC or Boc for tert-butyloxy carbonyl.

Synthetic Methods

The compounds and processes of the present invention will be better understood in connection with the following synthetic schemes which illustrate the methods by which the compounds of the invention may be prepared.

Compounds of the present invention can be made via a replacement procedure described generally in the following scheme:

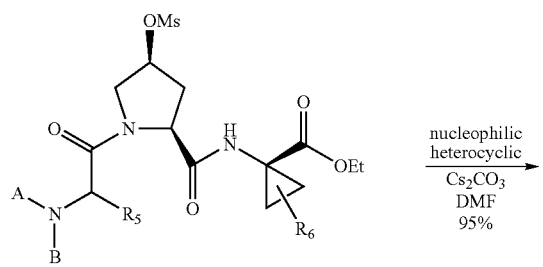

or via Mitsunobu conditions described generally in the following scheme:

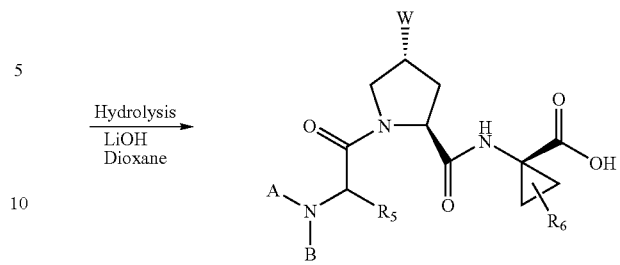

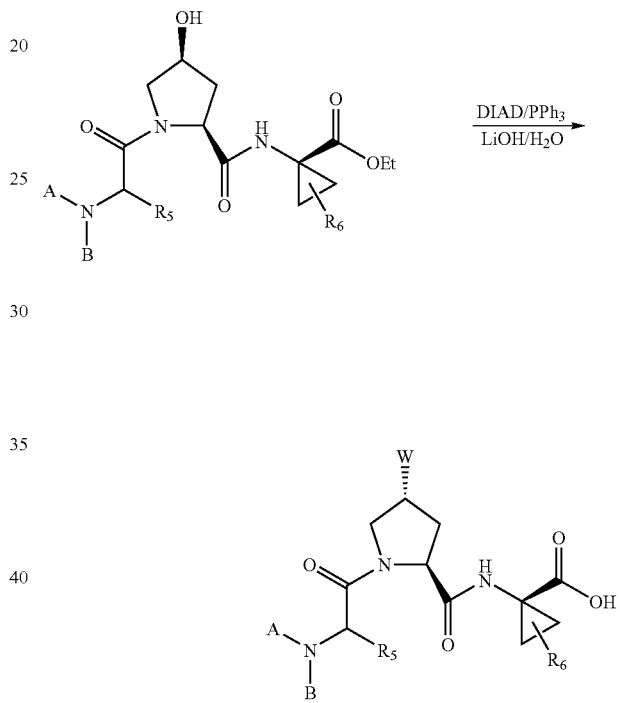

For further details on the Mitsunobu reaction see O. Mitsunobu, *Synthesis* 1981, 1–28; D. L. Hughes, *Org. React.* 29, 1–162 (1983); D. L. Hughes, *Organic Preparations and Procedures Int.* 28, 127–164 (1996); and J. A. Dodge, S. A. Jones, *Recent Res. Dev. Org. Chem.* 1, 273–283 (1997).

EXAMPLES

The compounds and processes of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims A. Synthesis of the Tripeptide Precursor

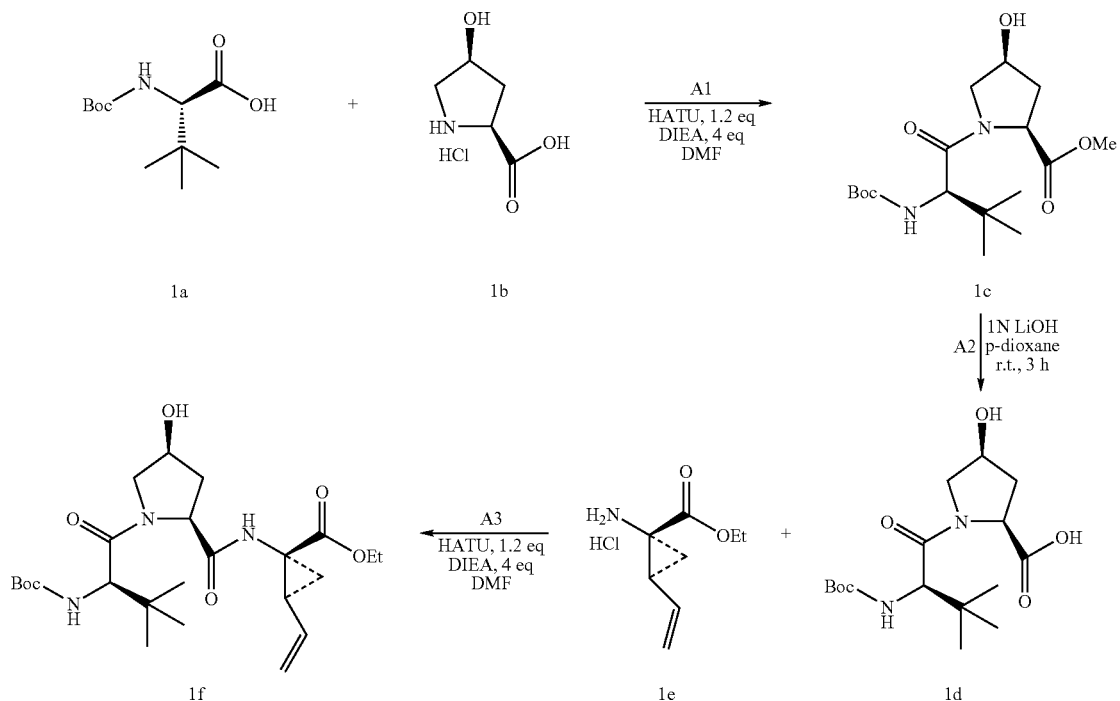

A1. To a solution of Boc-L-t-butyl glycine 1a, (1.16 g, 5 mmol) and commercially available cis-L-hydroxyproline methyl ester 1b (1.09 g, 6 mmol) in 15 ml DMF, DIEA (4 ml, 4 eq.) and HATU (4 g, 2 eq) were added. The coupling was carried out at 0° C. over a period of 1 hour. The reaction mixture was diluted with 100 mL EtOAc and subsequently the extract was washed with 5% citric acid (2×20 ml), water (2×20 ml), 1M NaHCO$_3$ (4×20 ml), and brine (2×10 ml), respectively. The organic phase was dried over anhydrous Na$_2$SO$_4$ and evaporated in vacuo, affording dipeptide 1c (1.91 g, 95.8%) identified by HPLC (Rt is 8.9 min, 30–70%, 90% B), and MS (found 421.37, M+Na$^+$).

A2. A solution of dipeptide 1c (1.91 g) dissolved in 15 mL of dioxane and 15 mL of aqueous 1 N LiOH solution was carried out at room temperature for 4 hours. The reaction mixture was acidified by 5% citric acid and extracted with 100 mL EtOAc, and washed with water (2×20 ml), 1M NaHCO$_3$ (2×20 ml), and brine (2×20 ml), respectively. The organic phase was dried over anhydrous Na$_2$SO$_4$ and then concentrated in vacuo, yielding the free carboxylic acid compound 1d (1.79 g, 97%), which was used in step 1C in its crude form.

A3. To a solution of free acid 1d obtained above (1.77, 4.64 mmol) in 5 ml DMF, D-β-vinyl cyclopropane amino acid ethyl ester 1e (0.95 g, 5 mmol), DWEA (4 ml, 4 eq.), and HATU (4 g, 2 eq) were added. The coupling was carried out at 0° C. over a period of 5 hours. The reaction mixture was then diluted with 80 mL EtOAc, and washed with 5% citric acid (2×20 ml), water (2×20 ml), 1M NaHCO$_3$ (4×20 ml), and brine (2×10 ml), respectively. The organic phase was dried over anhydrous Na$_2$SO$_4$ and then concentrated in vacuo. The residue was purified by silica gel flash chromatography using different ratios of hexanes:EtOAc as elution phase (5:1→3:1→1:1→1:2→1:5). Linear tripeptide 1f was isolated as an oil after removal of the elution solvents (1.59 g, 65.4%), identified by HPLC (Rt is 11.43 min) and MS (found 544.84, M+Na$^+$).

B. Synthesis of the Tripeptide Precursor Mesylate (a Compound of Formula I, wherein A is tBOC, B is H, G is OEt, W is OMs, R$_5$ is t-butyl, and R$_6$ is Vinyl.

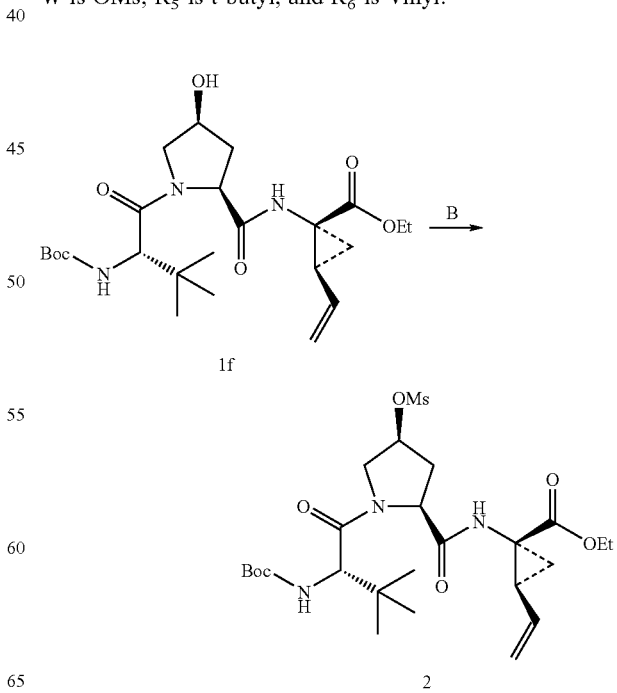

To a solution of tripeptide precursor 1f (500 mg, 1.01 mmol) and DIEA (0.4 ml, 2 mmol) in 2.0 ml DCM, mesylate chloride (0.1 ml) was added slowly at 0° C. at which the reaction was stirred for 3 hours. The resulting reaction mixture was then extracted with 30 mL EtOAc and washed with 5% citric acid (2×10 ml), water (2×10 ml), 1M NaHCO$_3$ (2×10 ml), and brine (2×10 ml), respectively. The organic phase was dried over anhydrous Na$_2$SO$_4$ and evaporated in vacuo, yielding the title compound mesylate which was used in subsequent steps in its crude form.

C. Replacement Method Reaction Conditions

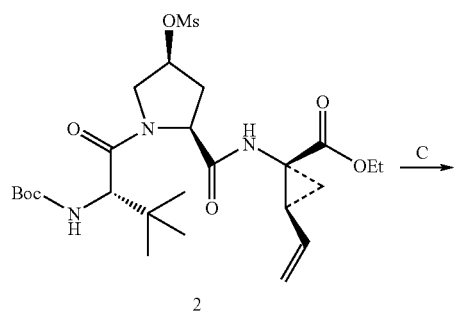

2

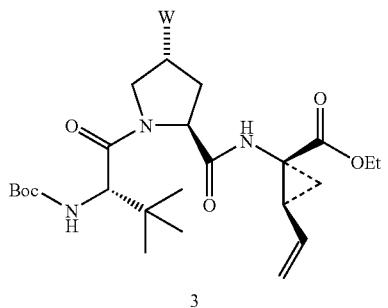

3

Compounds of formula 3 may be prepared by dissolving 0.041 mmol of compound 2 and 0.123 mmol of a nucleophilic heterocycle (W) in 3 ml of DMF, adding 0.246 mmol of cesium carbonate (80 mg), and reacting at 70° C. for 12 hours. The reaction mixture is then extracted with EtOAc and washed with 1M sodium bicarbonate (2×30 ml) and water (2×30 ml). The resulting organic solution is concentrated in vacuo to dryness.

D. Mitsunobu Reaction Conditions

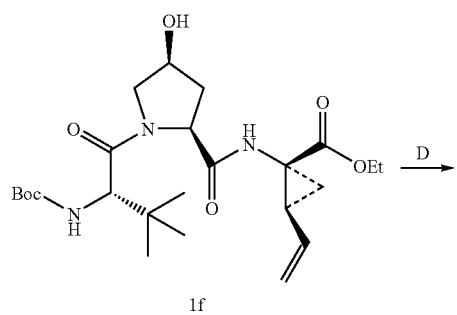

1f

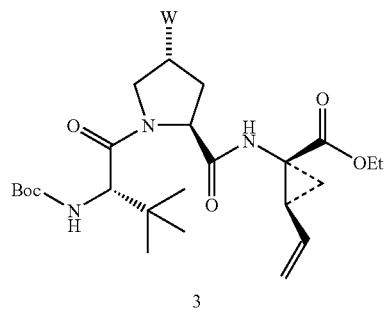

3

To a mixture of the tri-peptide compound 1f (185 mg, 0.38 mmol), a substituted or unsubstituted nucleophilic heterocycle (W) (0.38 mmol) and triphenylphosphine (197 mg, 0.75 mmol) in THF (5 mL) is added DIAD (148 μL, 0.75 mmol) dropwise at 0° C. After stirring at 0° C. for 15 min., the solution is warmed to room temperature and is further stirred for 16 hours. The mixture is then concentrated in vacuo and the residue is purified by column chromatography eluting with 40% ethyl acetate-hexane to give 235 mg (86%) of compound 3.

The following example compounds of the present invention are made via Mitsunobu or the replacement methods delineated in the above examples and synthetic schemes from precursors 1f or 2.

Example compounds 1–133 are prepared from the mesylate compound 2 and the appropriate substituted or unsubstituted heterocycle via the replacement method delineated above:

Example 1

Compound of formula I, wherein A is tBOC, B is H, G is OEt, W is OMs, R$_3$ is t-butyl, and R$_4$ is vinyl;

Example 2

Compound of Formula I, wherein A is tBOC, B is H, G is OH, W is

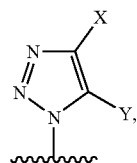

X is H, Y is 4-t-butylphenyl, m=s=1, R$_5$ is t-butyl, and R$_6$ is vinyl;

Example 3

Compound of Formula I, wherein A is tBOC, B is H, G is OH, W is

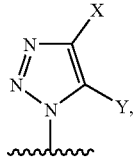

X is 4-t-butylphenyl, Y is H, m=s=1, R$_5$ is t-butyl, and R$_6$ is vinyl;

Example 4

Compound of Formula I, wherein A is tBOC, B is H, G is OH, W is

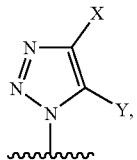

X and Y are taken together is phenyl, m=s=1, R$_5$ is t-butyl, and R$_6$ is vinyl;

Example 5

Compound of Formula I, wherein A is tBOC, B is H, G is OH, W is

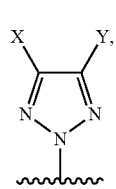

X and Y taken together is phenyl, m=s=1, R$_5$ is t-butyl, and R$_6$ is vinyl;

Example 6

Compound of Formula I, wherein A is tBOC, B is H, G is OH, W is

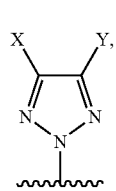

X is Y is phenyl, m=s=1, R$_5$ is t-butyl, and R$_6$ is vinyl;

Example 7

Compound of Formula I, wherein A is tBOC, B is H, G is OEt, W is

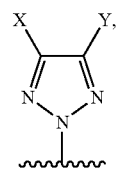

X is Y is phenyl, m=s=1, R$_5$ is t-butyl, and R$_6$ is vinyl;

Example 8

Compound of Formula I, wherein A is tBOC, B is H, G is OH, W is

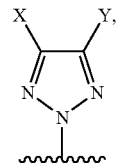

X is Y is phenyl, m=s=1, R$_5$ is t-butyl, and R$_6$ is vinyl;

Example 9

Compound of Formula I, wherein A is tBOC, B is H, G is OH, W is

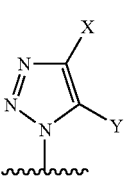

X is Y is phenyl, m=s=1, R$_5$ is t-butyl, and R$_6$ is vinyl;

Example 10

Compound of Formula I, wherein A is tBOC, B is H, G is OH, W is

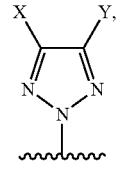

X is n-propyl, Y is phenyl, m=s=1, R$_5$ is t-butyl, and R$_6$ is vinyl;

Example 11

Compound of Formula I, wherein A is tBOC, B is H, G is OH, W is

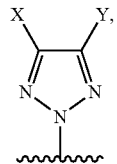

X is m-methoxyphenyl, Y is p-methoxyphenyl, m=s=1, $R_5$ is t-butyl, and $R_6$ is vinyl;

Example 12

Compound of Formula I, wherein A is tBOC, B is H, G is OH, W is

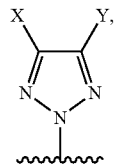

X is m-bromophenyl, Y is p-methoxyphenyl, m=s=1, $R_5$ is t-butyl, and $R_6$ is vinyl;

Example 13

Compound of Formula I, wherein A is tBOC, B is H, G is OH, W is

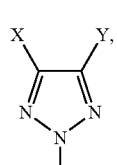

X is 1-napthyl, Y is p-methoxyphenyl, m=s=1, $R_5$ is t-butyl, and $R_6$ is vinyl;

Example 14

Compound of Formula I, wherein A is tBOC, B is H, G is OH, W is

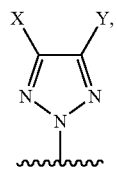

X is 2-thienyl, Y is p-methoxyphenyl, m=s=1, $R_5$ is t-butyl, and $R_6$ is vinyl;

Example 15

Compound of Formula I, wherein A is tBOC, B is H, G is OH, W is

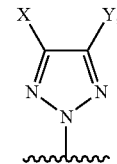

X is 3-thienyl, Y is p-methoxyphenyl, m=s=1, $R_5$ is t-butyl, and $R_6$ is vinyl;

Example 16

Compound of Formula I, wherein A is tBOC, B is H, G is OH, W is

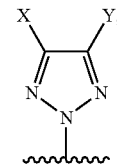

X is 4-pyrazolyl, Y is p-methoxyphenyl, m=s=1, $R_5$ is t-butyl, and $R_6$ is vinyl;

Example 17

Compound of Formula I, wherein A is tBOC, B is H, G is OH, W is

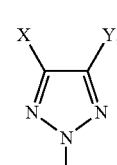

X is 3-pyridyl, Y is p-methoxyphenyl, m=s=1, $R_5$ is t-butyl, and $R_6$ is vinyl;

Example 18

Compound of Formula I, wherein A is tBOC, B is H, G is OH, W is

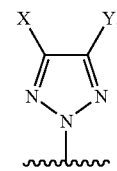

X is 2-pyridyl, Y is p-methoxyphenyl, m=s=1, $R_5$ is t-butyl, and $R_6$ is vinyl;

Example 19

Compound of Formula I, wherein A is tBOC, B is H, G is OH, W is

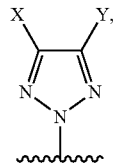

X is 2-thiazolyl, Y is p-methoxyphenyl, m=s=1, $R_5$ is t-butyl, and $R_6$ is vinyl;

Example 20

Compound of Formula I, wherein A is tBOC, B is H, G is OH, W is

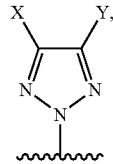

X is benzyl, Y is phenyl, m=s=1, $R_5$ is t-butyl, and $R_6$ is vinyl;

Example 21

Compound of Formula I, wherein A is tBOC, B is H, G is OH, W is

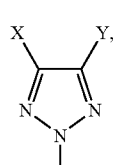

X is n-butyl, Y is phenyl, m=s=1, $R_5$ is t-butyl, and $R_6$ is vinyl;

Example 22

Compound of Formula I, wherein A is tBOC, B is H, G is OH, W is

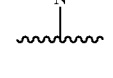

X is n-propyl, Y is n-propyl, m=s=1, $R_5$ is t-butyl, and $R_6$ is vinyl;

Example 23

Compound of Formula I, wherein A is tBOC, B is H, G is OH, W is

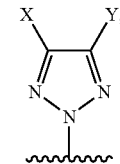

X is 4-(N,N-dimethylamino)phenyl, Y is phenyl, m=s=1, $R_5$ is t-butyl, and $R_6$ is vinyl;

Example 24

Compound of Formula I, wherein A is tBOC, B is H, G is OH, W is

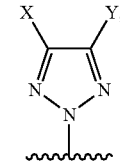

X is (N,N-diethylamino)methyl, Y is phenyl, m=s=1, $R_5$ is t-butyl, and $R_6$ is vinyl;

Example 25

Compound of Formula I, wherein A is tBOC, B is H, G is OH, W is

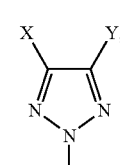

X is N,N-diethylaminocarbonyl, Y is phenyl, m=s=1, $R_5$ is t-butyl, and $R_6$ is vinyl;

Example 26

Compound of Formula I, wherein A is tBOC, B is H, G is OH, W is

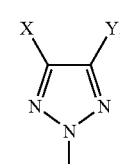

X is m-chlorophenyl, Y is 4-ethoxyphenyl, m=s=1, $R_5$ is t-butyl, and $R_6$ is vinyl;

Example 27

Compound of Formula I, wherein A is tBOC, B is H, G is OH, W is

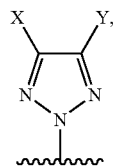

X is 2-phenylethenyl, Y is phenyl, m=s=1, $R_5$ is t-butyl, and $R_6$ is vinyl;

Example 28

Compound of Formula I, wherein A is tBOC, B is H, G is OH, W is 5,6-methylbenzotriazole, m=s=1, $R_5$ is t-butyl, and $R_6$ is vinyl;

Example 29

Compound of Formula I, wherein A is tBOC, B is H, G is OH, W is

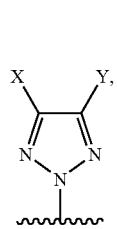

X is N-ethylaminocarbonyl, Y is phenyl, m=s=1, $R_5$ is t-butyl, and $R_6$ is vinyl;

Example 30

Compound of Formula I, wherein A is —(C=O)—O—$R_1$, wherein $R_1$ is cyclopentyl, B is H, G is OH, W is

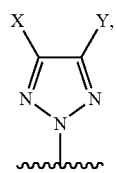

X is phenyl, Y is phenyl, m=s=1, $R_5$ is t-butyl, and $R_6$ is vinyl;

Example 31

Compound of Formula I, wherein A is —(C=O)—O—$R_1$, wherein $R_1$ is cyclobutyl, B is H, G is OH, W is

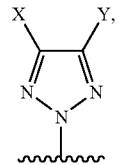

X is phenyl, Y is phenyl, m=s=1, $R_5$ is t-butyl, and $R_6$ is vinyl;

Example 32

Compound of Formula I, wherein A is —(C=O)—O—$R_1$, wherein $R_1$ is cyclohexyl, B is H, G is OH, W is

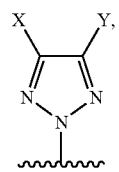

X is phenyl, Y is phenyl, m=s=1, $R_5$ is t-butyl, and $R_6$ is vinyl;

Example 33

Compound of Formula I, wherein A is —(C=O)—O—$R_1$, wherein $R_1$ is

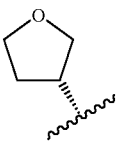

B is H, G is OH, W is

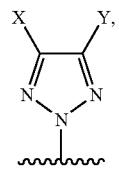

X is phenyl, Y is phenyl, m=s=1, $R_5$ is t-butyl, and $R_6$ is vinyl;

Example 34

Compound of Formula I, wherein A is —(C=O)—O—$R_1$, wherein $R_1$ is

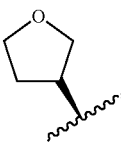

B is H, G is OH, W is

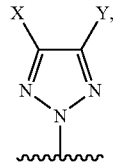

X is phenyl, Y is phenyl, m=s=1, $R_5$ is t-butyl, and $R_6$ is vinyl;

Example 35

Compound of Formula I, wherein A is —(C=O)—O—$R_1$, wherein $R_1$ is

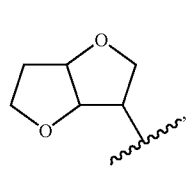

B is H, G is OH, W is

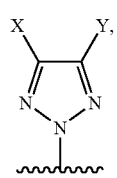

X is phenyl, Y is phenyl, m=s=1, $R_5$ is t-butyl, and $R_6$ is vinyl;

Example 36

Compound of Formula I, wherein A is —(C=O)—$R_1$, wherein $R_1$ is cyclopentyl, B is H, G is OH, W is

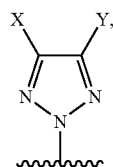

X is phenyl, Y is phenyl, m=s=1, $R_5$ is t-butyl, and $R_6$ is vinyl;

Example 37

Compound of Formula I, wherein A is —(C=O)—NH—$R_1$, wherein $R_1$ is cyclopentyl, B is H, G is OH, W is

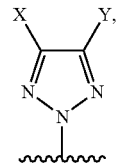

X is phenyl, Y is phenyl, m=s=1, $R_5$ is t-butyl, and $R_6$ is vinyl;

Example 38

Compound of Formula I, wherein A is —(C=S)—NH—$R_1$, wherein $R_1$ is cyclopentyl, B is H, G is OH, W is

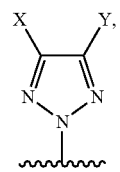

X is phenyl, Y is phenyl, m=s=1, $R_5$ is t-butyl, and $R_6$ is vinyl;

Example 39

Compound of Formula I, wherein A is —S(O)$_2$—$R_1$, wherein $R_1$ is cyclopentyl, B is H, G is OH, W is

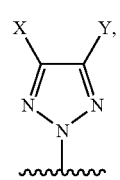

X is phenyl, Y is phenyl, m=s=1, $R_5$ is t-butyl, and $R_6$ is vinyl;

Example 40

Compound of Formula I, wherein A is —(C=O)—O—$R_1$, $R_1$ is cyclopentyl, B is H, G is —O-phenethyl, W is

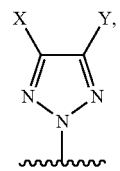

X is phenyl, Y is phenyl, m=s=1, $R_5$ is t-butyl, and $R_6$ is vinyl;

Example 41

Compound of Formula I, wherein A is —(C=O)—O—R$_1$, R$_1$ is cyclopentyl, B is H, G is —NH-phenethyl, W is

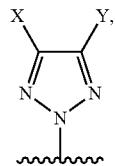

X is phenyl, Y is phenyl, m=s=1, R$_5$ is t-butyl, and R$_6$ is vinyl;

Example 42

Compound of Formula I, wherein A is —(C=O)—O—R$_1$, R$_1$ is cyclopentyl, B is H, G is —NHS(O)$_2$-phenethyl, W is

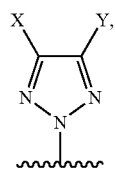

X is phenyl, Y is phenyl, m=s=1, R$_5$ is t-butyl, and R$_6$ is vinyl;

Example 43

Compound of Formula I, wherein A is —(C=O)—O—R$_1$, R$_1$ is cyclopentyl, B is H, G is —(C=O)—OH, W is

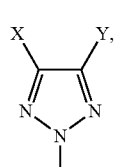

X is phenyl, Y is phenyl, m=s=1, R$_5$ is t-butyl, and R$_6$ is vinyl;

Example 44

Compound of Formula I, wherein A is —(C=O)—O—R$_1$, R$_1$ is cyclopentyl, B is H, G is —(C=O)—O-phenethyl, W is

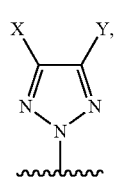

X is phenyl, Y is phenyl, m=s=1, R$_5$ is t-butyl, and R$_6$ is vinyl;

Example 45

Compound of Formula I, wherein A is —(C=O)—O—R$_1$, R$_1$ is cyclopentyl, B is H, G is —(C=O)—NH-phenethyl, W is

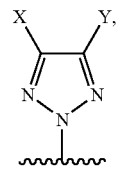

X is phenyl, Y is phenyl, m=s=1, R$_5$ is t-butyl, and R$_6$ is vinyl;

Example 46

Compound of Formula I, wherein A is —(C=O)—O—R$_1$, R$_1$ is cyclopentyl, B is H, G is —(C=O)—NH—S(O)$_2$-benzyl, W is

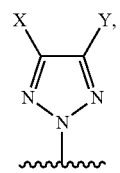

X is phenyl, Y is phenyl, m=s=1, R$_5$ is t-butyl, and R$_6$ is vinyl;

Example 47

Compound of Formula I, wherein A is tBOC, B is H, G is OH, W is

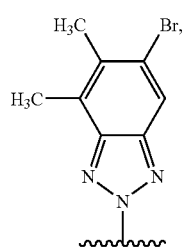

m=s=1, R$_5$ is t-butyl, and R$_6$ is vinyl;

Example 48

Compound of Formula I, wherein A is tBOC, B is H, G is OH, W is

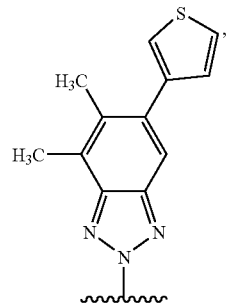

m=s=1, R$_5$ is t-butyl, and R$_6$ is vinyl; or

Example 49

Compound of Formula I, wherein A is tBOC, B is H, G is OH, W is

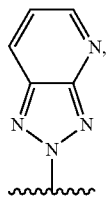

m=s=1, R$_5$ is t-butyl, and R$_6$ is vinyl;

Example 50

Compound of Formula I, wherein A is tBOC, B is H, G is OH, W is

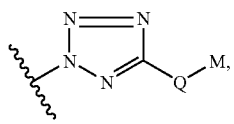

Q is absent, M is phenyl, m=s=1, R$_5$ is t-butyl, and R$_6$ is vinyl;

Example 51

Compound of Formula I, wherein A is tBOC, B is H, G is OH, W is

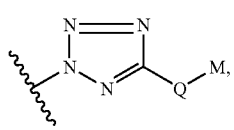

Q is absent, M is 2-bromophenyl, m=s=1, R$_5$ is t-butyl, and R$_6$ is vinyl;

Example 52

Compound of Formula I, wherein A is tBOC, B is H, G is OH, W is

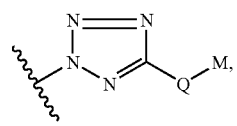

Q is absent, M is 3-bromophenyl, m=s=1, R$_5$ is t-butyl, and R$_6$ is vinyl;

Example 53

Compound of Formula I, wherein A is tBOC, B is H, G is OH, W is

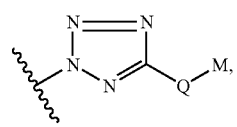

Q is absent, M is 4-bromophenyl, m=s=1, R$_5$ is t-butyl, and R$_6$ is vinyl;

Example 54

Compound of Formula I, wherein A is tBOC, B is H, G is OH, W is

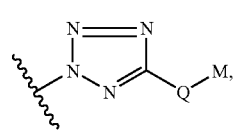

Q is absent, M is S-Bromo-2-thienyl, m=s=1, R$_5$ is t-butyl, and R$_6$ is vinyl;

Example 55

Compound of Formula I, wherein A is tBOC, B is H, G is OH, W is

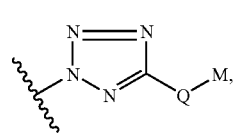

Q is absent, M is 2-bromo-4-pyridyl, m=s=1, R$_5$ is t-butyl, and R$_6$ is vinyl;

Example 56

Compound of Formula I, wherein A is tBOC, B is H, G is OH, W is

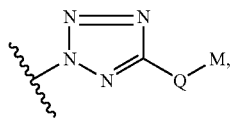

Q is absent, M is 2-biphenyl, m=s=1, $R_5$ is t-butyl, and $R_6$ is vinyl;

Example 57

Compound of Formula I, wherein A is tBOC, B is H, G is OH, W is

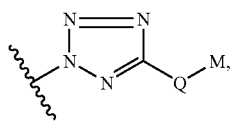

Q is absent, M is 3-biphenyl, m=s=1, $R_5$ is t-butyl, and $R_6$ is vinyl;

Example 58

Compound of Formula I, wherein A is tBOC, B is H, G is OH, W is

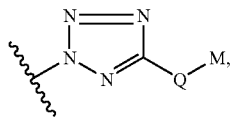

Q is absent, M is 4-biphenyl, m=s=1, $R_5$ is t-butyl, and $R_6$ is vinyl;

Example 59

Compound of Formula I, wherein A is tBOC, B is H, G is OH, W is

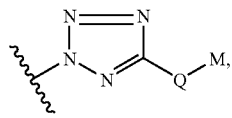

Q is absent, M is 3-(3-thienyl)phenyl, m=s=1, $R_5$ is t-butyl, and $R_6$ is vinyl;

Example 60

Compound of Formula I, wherein A is tBOC, B is H, G is OH, W is

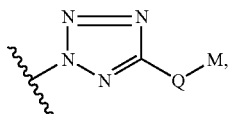

Q is absent, M is 3-(p-trifluoromethoxyphenyl)phenyl, m=s=1, $R_5$ is t-butyl, and $R_6$ is vinyl;

Example 61

Compound of Formula I, wherein A is tBOC, B is H, G is OH, W is

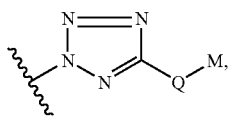

Q is absent, M is 3-(p-cyanophenyl)phenyl, m=s=1, $R_5$ is t-butyl, and $R_6$ is vinyl;

Example 62

Compound of Formula I, wherein A is tBOC, B is H, G is OH, W is

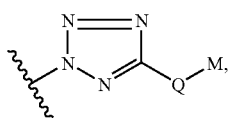

Q is absent, M is 4-(3-thienyl)phenyl, m=s=1, $R_5$ is t-butyl, and $R_6$ is vinyl;

Example 63

Compound of Formula I, wherein A is tBOC, B is H, G is OH, W is

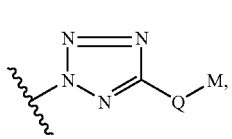

is absent, M is 4-(p-trifluoromethoxyphenyl)phenyl, m=s=1, $R_5$ is t-butyl, and $R_6$ is vinyl;

Example 64

Compound of Formula I, wherein A is tBOC, B is H, G is OH, W is

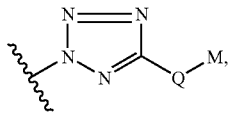

Q is absent, M is 4-(p-cyanophenyl)phenyl, m=s=1, $R_5$ is t-butyl, and $R_6$ is vinyl;

Example 65

Compound of Formula I, wherein A is tBOC, B is H, G is OH, W is

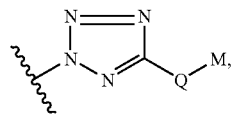

Q is absent, M is 5-phenyl-2-thienyl, m=s=1, $R_5$ is t-butyl, and $R_6$ is vinyl;

Example 66

Compound of Formula I, wherein A is tBOC, B is H, G is OH, W is

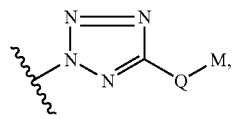

Q is absent, M is 5-phenyl-3-pyridyl, m=s=1, $R_5$ is t-butyl, and $R_6$ is vinyl;

Example 67

Example 68

Compound of Formula I, wherein A is tBOC, B is H, G is OEt, W is

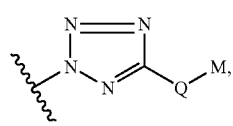

Q is absent, M is 3-chloro-4-hydroxyphenyl, m=s=1, $R_5$ is t-butyl, and $R_6$ is vinyl;

Example 69

Compound of Formula I, wherein A is tBOC, B is H, G is OH, W is

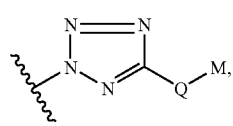

Q is absent, M is 3-chloro-4-hydroxyphenyl, m=s=1, $R_5$ is t-butyl, and $R_6$ is vinyl;

Example 70

Compound of Formula I, wherein A is tBOC, B is H, G is OH, W is

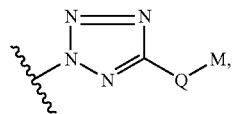

Q is absent, M is 3-bromo-4-hydroxyphenyl, m=s=1, $R_5$ is t-butyl, and $R_6$ is vinyl;

Example 71

Compound of Formula I, wherein A is tBOC, B is H, G is OH, W is

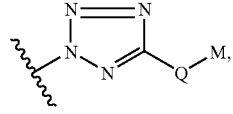

Q is absent, M is 2-methyl-4-bromophenyl, m=s=1, $R_5$ is t-butyl, and $R_6$ is vinyl;

Example 72

Compound of Formula I, wherein A is tBOC, B is H, G is OH, W is

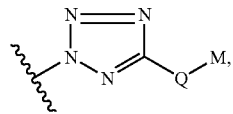

Q is absent, M is 3-methyl-4-bromophenyl, m=s=1, $R_5$ is t-butyl, and $R_6$ is vinyl;

Example 73

Compound of Formula I, wherein A is tBOC, B is H, G is OH, W is

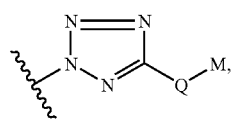

Q is absent, M is n-propyl, m=s=1, $R_5$ is t-butyl, and $R_6$ is vinyl;

Example 74

Compound of Formula I, wherein A is tBOC, B is H, G is OH, W is

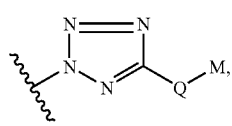

Q is absent, M is n-butyl, m=s=1, $R_5$ is t-butyl, and $R_6$ is vinyl;

Example 75

Compound of Formula I, wherein A is tBOC, B is H, G is OH, W is

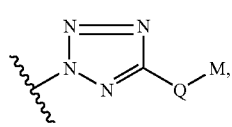

Q is absent, M is 4-ethoxyphenyl, m=s=1, $R_5$ is t-butyl, and $R_6$ is vinyl;

Example 76

Compound of Formula I, wherein A is tBOC, B is H, G is OH, W is

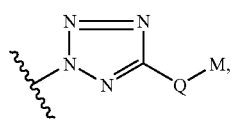

Q is absent, M is 4-propoxyphenyl, m=s=1, $R_5$ is t-butyl, and $R_6$ is vinyl;

Example 77

Compound of Formula I, wherein A is tBOC, B is H, G is OH, W is

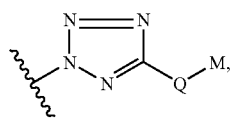

Q is absent, M is 4-butoxyphenyl, m=s=1, $R_5$ is t-butyl, and $R_6$ is vinyl;

Example 78

Compound of Formula I, wherein A is tBOC, B is H, G is OH, W is

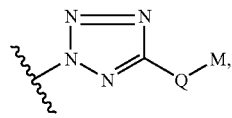

Q is absent, M is 3-methoxyphenyl, m s=1, $R_5$ is t-butyl, and $R_6$ is vinyl;

Example 79

Compound of Formula I, wherein A is tBOC, B is H, G is OH, W is

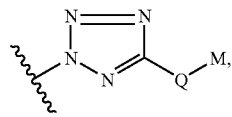

Q is absent, M is 3,4-dimethoxyphenyl, m=s=1, $R_5$ is t-butyl, and $R_6$ is vinyl;

Example 80

Compound of Formula I, wherein A is tBOC, B is H, G is OH, W is

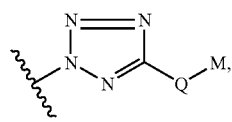

Q is absent, M is 4-methoxy-1-naphthyl, m=s=1, $R_5$ is t-butyl, and $R_6$ is vinyl;

Example 81

Compound of Formula I, wherein A is tBOC, B is H, G is OH, W is

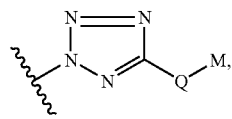

Q is absent, M is 4-phenoxyphenyl, m=s=1, $R_5$ is t-butyl, and $R_6$ is vinyl;

Example 82

Compound of Formula I, wherein A is tBOC, B is H, G is OH, W is

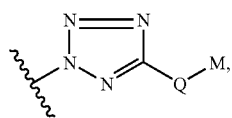

Q is absent, M is benzyl, m=s=1, $R_5$ is t-butyl, and $R_6$ is vinyl;

Example 83

Compound of Formula I, wherein A is tBOC, B is H, G is OH, W is

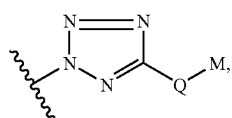

Q is absent, M is p-phenylbenzyl, m=s=1, $R_5$ is t-butyl, and $R_6$ is vinyl;

Example 84

Compound of Formula I, wherein A is tBOC, B is H, G is OH, W is

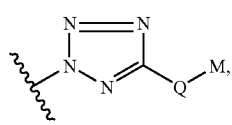

Q is absent, M is 3-chlorophenyl, m=s=1, $R_5$ is t-butyl, and $R_6$ is vinyl;

Example 85

Compound of Formula I, wherein A is tBOC, B is H, G is OH, W is

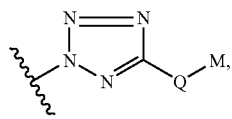

Q is absent, M is 3-fluorophenyl, m=s=1, $R_5$ is t-butyl, and $R_6$ is vinyl;

Example 86

Compound of Formula I, wherein A is tBOC, B is H, G is OH, W is

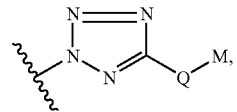

Q is absent, M is 3-methoxyphenyl, m=s=1, $R_5$ is t-butyl, and $R_6$ is vinyl;

Example 87

Compound of Formula I, wherein A is tBOC, B is H, G is OH, W is

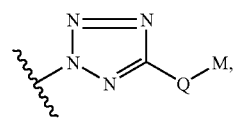

Q is absent, M is 3-phenoxyphenyl, m=s=1, $R_5$ is t-butyl, and $R_6$ is vinyl;

Example 88

Compound of Formula I, wherein A is tBOC, B is H, G is OH, W is

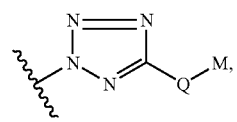

Q is absent, M is 3-benzyloxyphenyl, m=s=1, $R_5$ is t-butyl, and $R_6$ is vinyl;

Example 89

Compound of Formula I, wherein A is tBOC, B is H, G is OH, W is

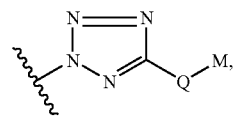

Q is absent, M is 3-trifluormethylphenyl, m=s=1, $R_5$ is t-butyl, and $R_6$ is vinyl;

Example 90

Compound of Formula I, wherein A is tBOC, B is H, G is OH, W is

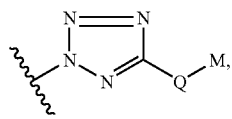

Q is absent, M is 4-bromophenyl, m=s=1, R$_5$ is t-butyl, and R$_6$ is vinyl;

Example 91

Compound of Formula I, wherein A is tBOC, B is H, G is OH, W is

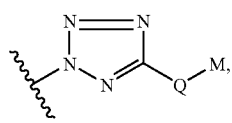

Q is absent, M is 4-fluorophenyl, m=s=1, R$_5$ is t-butyl, and R$_6$ is vinyl;

Example 92

Compound of Formula I, wherein A is tBOC, B is H, G is OH, W is

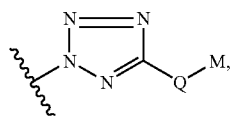

Q is absent, M is 4-methoxyphenyl, m=s=1, R$_5$ is t-butyl, and R$_6$ is vinyl;

Example 93

Compound of Formula I, wherein A is tBOC, B is H, G is OH, W is

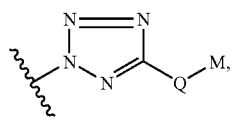

Q is absent, M is 4-ethoxyphenyl, m=s=1, R$_5$ is t-butyl, and R$_6$ is vinyl;

Example 94

Compound of Formula I, wherein A is tBOC, B is H, G is OH, W is

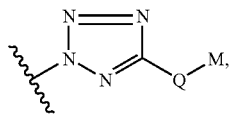

Q is absent, M is 4-trifluoromethylphenyl, m=s=1, R$_5$ is t-butyl, and R$_6$ is vinyl;

Example 95

Compound of Formula I, wherein A is tBOC, B is H, G is OH, W is

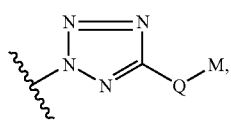

Q is absent, M is 3,5-di(trifluoromethyl)phenyl, m=s=1, R$_5$ is t-butyl, and R$_6$ is vinyl;

Example 96

Compound of Formula I, wherein A is tBOC, B is H, G is OH, W is

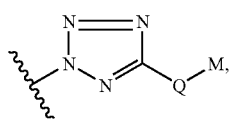

Q is absent, M is 4-(N,N-dimethylamino)-3,5-di(trifluoromethyl)phenyl, m=s=1, R$_5$ is t-butyl, and R$_6$ is vinyl;

Example 97

Compound of Formula I, wherein A is tBOC, B is H, G is OH, W is

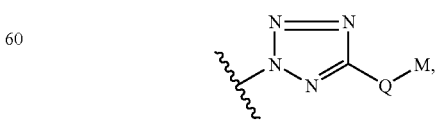

Q is absent, M is 2,4-dichlorophenyl, m=s=1, R$_5$ is t-butyl, and R$_6$ is vinyl;

Example 98

Compound of Formula I, wherein A is tBOC, B is H, G is OH, W is

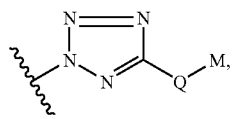

Q is absent, M is 3,5-dichlorophenyl, m=s=1, $R_5$ is t-butyl, and $R_6$ is vinyl;

Example 99

Compound of Formula I, wherein A is tBOC, B is H, G is OH, W is

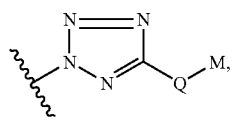

Q is absent, M is 3,4-dichlorophenyl, m=s=1, $R_5$ is t-butyl, and $R_6$ is vinyl;

Example 100

Compound of Formula I, wherein A is tBOC, B is H, G is OH, W is

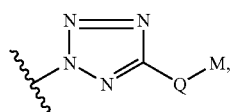

Q is absent, M is 2-pyridyl, m=s=1, $R_5$ is t-butyl, and $R_6$ is vinyl;

Example 101

Compound of Formula I, wherein A is tBOC, B is H, G is OH, W is

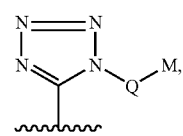

Q is absent, M is 2-pyridyl, m=s=1, $R_5$ is t-butyl, and $R_6$ is vinyl;

Example 102

Compound of Formula I, wherein A is tBOC, B is H, G is OH, W is

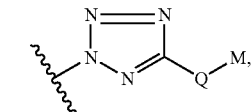

Q is absent, M is 3-pyridyl, m=s=1, $R_5$ is t-butyl, and $R_6$ is vinyl;

Example 103

Compound of Formula I, wherein A is tBOC, B is H, G is OH, W is

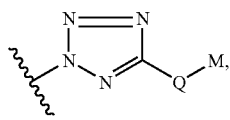

Q is absent, M is 4-pyridyl, m=s=1, $R_5$ is t-butyl, and $R_6$ is vinyl;

Example 104

Compound of Formula I, wherein A is tBOC, B is H, G is OH, W is

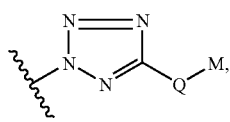

Q is absent, M is 4-methoxy-3-bromophenyl, m=s=1, $R_5$ is t-butyl, and $R_6$ is vinyl;

Example 105

Compound of Formula I, wherein A is tBOC, B is H, G is OH, W is

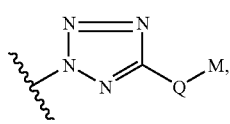

Q is absent, M is 4-(methylcyclopropane)phenyl, m=s=1, $R_5$ is t-butyl, and $R_6$ is vinyl;

Example 106

Compound of Formula I, wherein A is tBOC, B is H, G is OH, W is

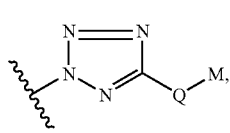

Q is absent, M is 3-chloro-4-(methylcyclopropane)phenyl, m=s=1, $R_5$ is t-butyl, and $R_6$ is vinyl;

Example 107

Compound of Formula I, wherein A is tBOC, B is H, G is OH, W is

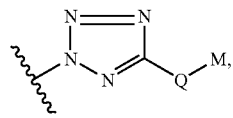

Q is absent, M is 3-chloro-4-methoxyphenyl, m=s=1, $R_5$ is t-butyl, and $R_6$ is vinyl;

Example 108

Compound of Formula I, wherein A is tBOC, B is H, G is OH, W is

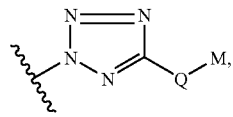

Q is absent, M is 3-chloro-4-ethoxyphenyl, m=s=1, $R_5$ is t-butyl, and $R_6$ is vinyl;

Example 109

Compound of Formula I, wherein A is tBOC, B is H, G is OH, W is

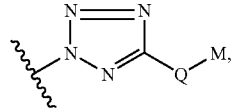

Q is absent, M is 3-bromo-4-ethoxyphenyl, m=s=1, $R_5$ is t-butyl, and $R_6$ is vinyl;

Example 110

Compound of Formula I, wherein A is tBOC, B is H, G is OH, W is

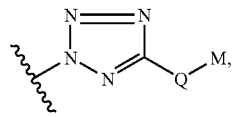

Q is absent, M is 3-chloro-4-(2-hydroxyethoxy)phenyl, m=s=1, $R_5$ is t-butyl, and $R_6$ is vinyl;

Example 111

Compound of Formula I, wherein A is tBOC, B is H, G is OH, W is

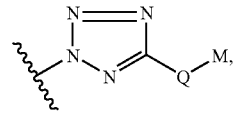

Q is absent, M is 3-bromo-4-(2-hydroxyethoxy)phenyl, m=s=1, $R_5$ is t-butyl, and $R_6$ is vinyl;

Example 112

Compound of Formula I, wherein A is tBOC, B is H, G is OH, W is

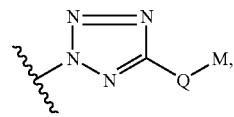

Q is absent, M is 3-chloro-4-(O-allyl)phenyl, m=s=1, $R_5$ is t-butyl, and $R_6$ is vinyl;

Example 113

Compound of Formula I, wherein A is tBOC, B is H, G is OH, W is

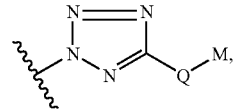

Q is absent, M is 3-bromo-4-(O-allyl)phenyl, m=s=1, $R_5$ is t-butyl, and $R_6$ is vinyl;

Example 114

Compound of Formula I, wherein A is tBOC, B is H, G is OH, W is

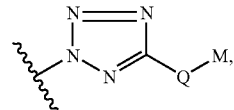

Q is absent, M is 3-chloro-4-(O—$CH_2SCH_3$)phenyl, m=s=1, $R_5$ is t-butyl, and $R_6$ is vinyl;

Example 115

Compound of Formula I, wherein A is tBOC, B is H, G is OH, W is

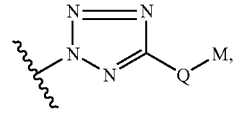

Q is absent, M is 3-chloro-4-(O—CH$_2$SCH$_3$)phenyl, m=s=1, R$_5$ is t-butyl, and R$_6$ is vinyl;

Example 116

Compound of Formula I, wherein A is tBOC, B is H, G is OH, W is

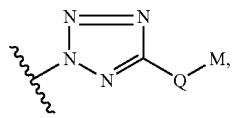

wherein Q' is —CH$_2$—, M is

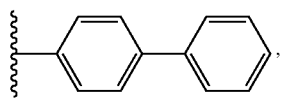

m=s=1, R$_5$ is t-butyl, and R$_6$ is vinyl;

Example 117

Compound of Formula I, wherein A is tBOC, B is H, G is OH, W is

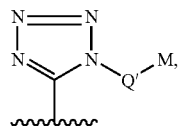

wherein Q' is —CH$_2$—, M is

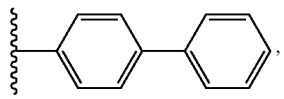

m=s=1, R$_5$ is t-butyl, and R$_6$ is vinyl;

Example 118

Compound of Formula I, wherein A is —(C=O)—O—R$_1$, wherein R$_1$ is cyclopentyl, B is H, G is OH, W is

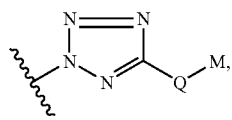

Q is absent, M is phenyl, m=s=1, R$_5$ is t-butyl, and R$_6$ is vinyl;

Example 119

Compound of Formula I, wherein A is —(C=O)—O—R$_1$, wherein R$_1$ is cyclobutyl, B is H, G is OH, W is

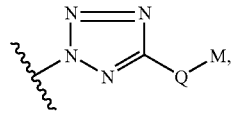

Q is absent, M is phenyl, m=s=1, R$_5$ is t-butyl, and R$_6$ is vinyl;

Example 120

Compound of Formula I, wherein A is —(C=O)—O—R$_1$, wherein R$_1$ is cyclohexyl, B is H, G is OH, W is

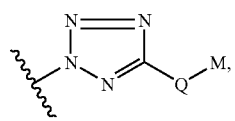

Q is absent, M is phenyl, m=s=1, R$_5$ is t-butyl, and R$_6$ is vinyl;

Example 121

Compound of Formula I, wherein A is —(C=O)—O—R$_1$, wherein R$_1$ is

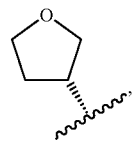

B is H, G is OH, W is

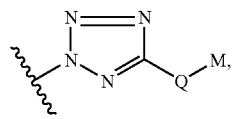

Q is absent, M is phenyl, m=s=1, R$_5$ is t-butyl, and R$_6$ is vinyl;

Example 122

Compound of Formula I, wherein A is —(C=O)—O—R$_1$, wherein R$_1$ is

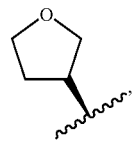

B is H, G is OH, W is

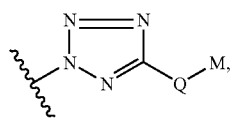

Q is absent, M is phenyl, m=s=1, R$_5$ is t-butyl, and R$_6$ is vinyl;

Example 123

Compound of Formula I, wherein A is —(C=O)—O—R$_1$, wherein R$_1$ is

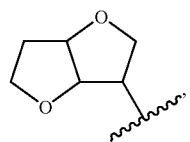

B is H, G is OH, W is

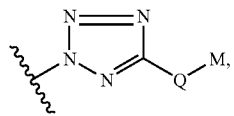

Q is absent, M is phenyl, m=s=1, R$_5$ is t-butyl, and R$_6$ is vinyl;

Example 124

Compound of Formula I, wherein A is —(C=O)—R$_1$, wherein R$_1$ is cyclopentyl, B is H, G is OH, W is

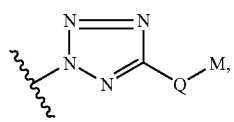

Q is absent, M is phenyl, m=s=1, R$_5$ is t-butyl, and R$_6$ is vinyl;

Example 125

Compound of Formula I, wherein A is —(C=O)—NH—R$_1$, wherein R$_1$ is cyclopentyl B is H, G is OH, W is

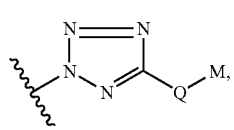

Q is absent, M is phenyl, m=s=1, R$_5$ is t-butyl, and R$_6$ is vinyl;

Example 126

Compound of Formula I, wherein A is —(C=S)—NH—R$_1$, wherein R$_1$ is cyclopentyl, B is H, G is OH, W is

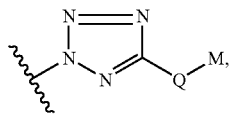

Q is absent, M is phenyl, m=s=1, R$_5$ is t-butyl, and R$_6$ is vinyl;

Example 127

Compound of Formula I, wherein A is —S(O)$_2$—R$_1$, wherein R$_1$ is cyclopentyl, B is H, G is OH, W is

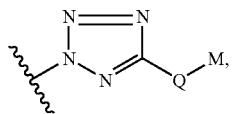

Q is absent, M is phenyl, m=s=1, R$_5$ is t-butyl, and R$_6$ is vinyl;

Example 128

Compound of Formula I, wherein A is tBOC, B is H, G is —O—CH$_2$-cyclopentyl, W is

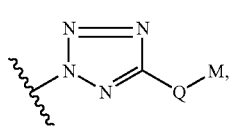

Q is absent, M is phenyl, m=s=1, R$_5$ is t-butyl, and R$_6$ is vinyl;

Example 129

Compound of Formula I, wherein A is tBOC, B is H, G is —NHS(O)$_2$—CH$_2$— cyclopentyl, W is

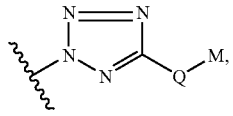

Q is absent, M is phenyl, m=s=1, R$_5$ is t-butyl, and R$_6$ is vinyl;

Example 130

Compound of Formula I, wherein A is tBOC, B is H, G is —(C=O)—CH$_2$— cyclopentyl, W is

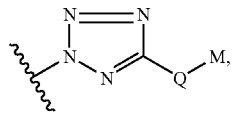

Q is absent, M is phenyl, m=s=1, R$_5$ is t-butyl, and R$_6$ is vinyl;

Example 131

Compound of Formula I, wherein A is tBOC, B is H, G is —(C=O)—O—CH$_2$— cyclopentyl, W is

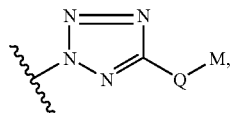

Q is absent, M is phenyl, m=s=1, R$_5$ is t-butyl, and R$_6$ is vinyl; and

Example 132

Compound of Formula I, wherein A is tBOC, B is H, G is —(C=O)—OH, W is

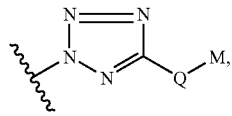

Q is absent, M is phenyl, m=s=1, R$_5$ is t-butyl, and R$_6$ is vinyl;

Example 133

Compound of Formula I, wherein A is tBOC, B is H, G is —(C=O)—NH—CH$_2$— cyclopentyl, W is

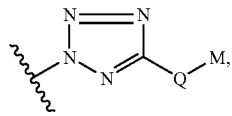

Q is absent, M is phenyl, m=s=1, R$_5$ is t-butyl, and R$_6$ is vinyl.

Example compounds 133–168 are prepared from the tri-peptide precursor compound if and the appropriate substituted or unsubstituted heterocycle via Mitsunobu conditions:

Example 134

Compound of Formula I, wherein A is tBOC, B is H, G is OEt, W is

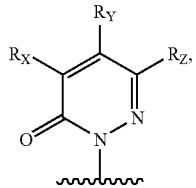

R$_X$ is bromo, R$_Y$ is bromo, R$_Z$ is hydrogen, m=s=1, R$_5$ is t-butyl, and R$_6$ is vinyl;

Example 135

Compound of Formula I, wherein A is tBOC, B is H, G is OEt, W is

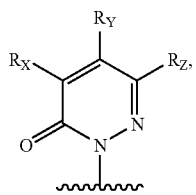

R$_X$ is thiophen-3-yl, R$_Y$ is thiophen-3-yl, R$_Z$ is hydrogen, m=s=1, R$_5$ is t-butyl, and R$_6$ is vinyl;

Example 136

Compound of Formula I, wherein A is tBOC, B is H, G is OH, W is

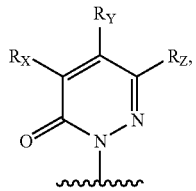

R$_X$ is thiophen-3-yl, R$_Y$ is thiophen-3-yl, R$_Z$ is hydrogen, m=s=1, R$_5$ is t-butyl, and R$_6$ is vinyl;

Example 137

Compound of Formula I, wherein A is tBOC, B is H, G is OH, W is

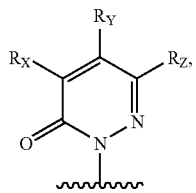

R$_X$ is phenyl, R$_Y$ is phenyl, R$_Z$ is hydrogen, m=s=1, R$_5$ is t-butyl, and R$_6$ is vinyl;

Example 138

Compound of Formula I, wherein A is tBOC, B is H, G is OH, W is

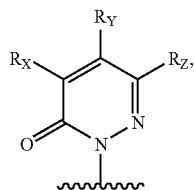

R$_X$ is 4-(trifluoromethoxy)phenyl, R$_Y$ is 4-(trifluoromethoxy)phenyl, R$_Z$ is hydrogen, m=s=1, R$_5$ is t-butyl, and R$_6$ is vinyl;

Example 139

Compound of Formula I, wherein A is tBOC, B is H, G is OH, W is

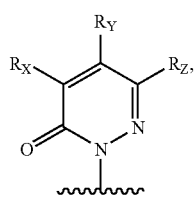

R$_X$ is 4-(methanesulfonyl)phenyl, R$_Y$ is 4-(methanesulfonyl)phenyl, R$_Z$ is hydrogen, m=s=1, R$_5$ is t-butyl, and R$_6$ is vinyl;

Example 140

Compound of Formula I, wherein A is tBOC, B is H, G is OH, W is

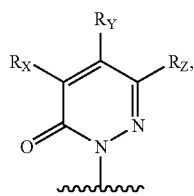

R$_X$ and R$_Y$ are each 4-(cyano)phenyl, R$_Z$ is hydrogen, m=s=1, R$_5$ is t-butyl, and R$_6$ is vinyl;

Example 141

Compound of Formula I, wherein A is tBOC, B is H, G is OH, W is

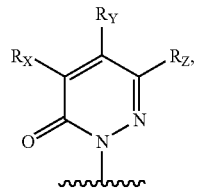

R$_X$ and R$_Y$ are each 3-pyridyl, R$_Z$ is hydrogen, m=s=1, R$_5$ is t-butyl, and R$_6$ is vinyl;

Example 142

Compound of Formula I, wherein A is tBOC, B is H, G is OH, W is

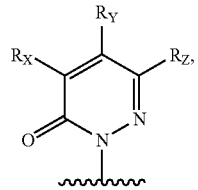

R$_X$ and R$_Y$ are each 4-(morpholin-4-yl-methanonyl)phenyl, R$_Z$ is hydrogen, m=s=1, R$_5$ is t-butyl, and R$_6$ is vinyl;

Example 143

Compound of Formula I, wherein A is tBOC, B is H, G is OH, W is

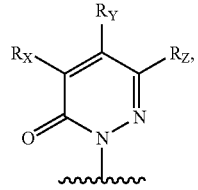

R$_X$ and R$_Y$ are each bromo, R$_Z$ is hydrogen, m=s=1, R$_5$ is t-butyl, and R$_6$ is vinyl;

Example 144

Compound of Formula I, wherein A is tBOC, B is H, G is OH, W is

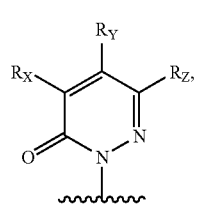

R$_X$ and R$_Y$ taken together is phenyl, R$_Z$ is 4-methoxyphenyl, m=s=1, R$_5$ is t-butyl, and R$_6$ is vinyl;

Example 145

Compound of Formula I, wherein A is tBOC, B is H, G is OH, W is

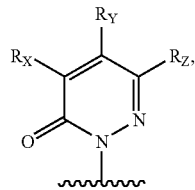

$R_X$ and $R_Y$ taken together is phenyl, $R_Z$ is 4-chlorophenyl, m=s=1, $R_5$ is t-butyl, and $R_6$ is vinyl;

Example 146

Compound of Formula I, wherein A is tBOC, B is H, G is OH, W is

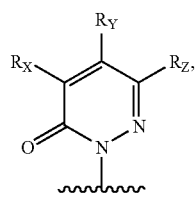

$R_X$ is 4-fluorophenyl, $R_Y$ is hydrogen, $R_Z$ is phenyl, m=s=1, $R_5$ is t-butyl, and $R_6$ is vinyl;

Example 147

Compound of Formula I, wherein A is tBOC, B is H, G is OH, W is

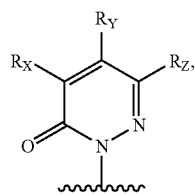

$R_X$ is hydrogen, $R_Y$ is 1-piperidyl, $R_Z$ is phenyl, m=s=1, $R_5$ is t-butyl, and $R_6$ is vinyl;

Example 148

Compound of Formula I, wherein A is tBOC, B is H, G is OEt, W is

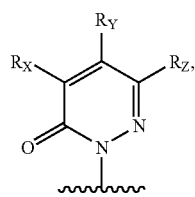

$R_X$ is hydrogen, $R_Y$ is bromo, $R_Z$ is phenyl, m=s=1, $R_5$ is t-butyl, and $R_6$ is vinyl;

Example 149

Compound of Formula I, wherein A is tBOC, B is H, G is OH, W is

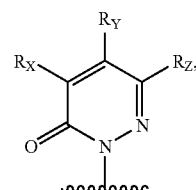

$R_X$ is hydrogen, $R_Y$ is thiophen-3-yl, $R_Z$ is phenyl, m=s=1, $R_5$ is t-butyl, and $R_6$ is vinyl;

Example 150

Compound of Formula I, wherein A is tBOC, B is H, G is OEt, W is

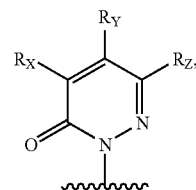

$R_X$ is bromo, $R_Y$ is pyrrolid-1-yl, $R_Z$ is hydrogen, m=s=1, $R_5$ is t-butyl, and $R_6$ is vinyl;

Example 151

Compound of Formula I, wherein A is tBOC, B is H, G is OH, W is

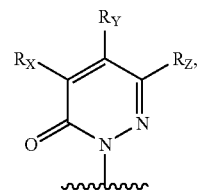

$R_X$ is thiophen-3-yl, $R_Y$ is pyrrolid-1-yl, $R_Z$ is hydrogen, m=s=1, $R_5$ is t-butyl, and $R_6$ is vinyl;

Example 152

Compound of Formula I, wherein A is tBOC, B is H, G is OEt, W is

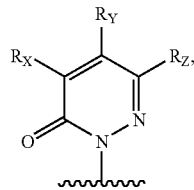

$R_X$ is bromo, $R_Y$ is azido, $R_Z$ is hydrogen, m=s=1, $R_5$ is t-butyl, and $R_6$ is vinyl;

Example 153

Compound of Formula I, wherein A is tBOC, B is H, G is OEt, W is

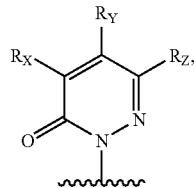

$R_X$ is thiophen-3-yl, $R_Y$ is azido, $R_Z$ is hydrogen, m=s=1, $R_5$ is t-butyl, and $R_6$ is vinyl;

Example 154

Compound of Formula I, wherein A is tBOC, B is H, G is OH, W is

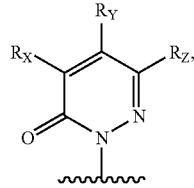

$R_X$ is thiophen-3-yl, $R_Y$ is azido, $R_Z$ is hydrogen, m=s=1, $R_5$ is t-butyl, and $R_6$ is vinyl;

Example 155

Compound of Formula I, wherein A is tBOC, B is H, G is OH, W is

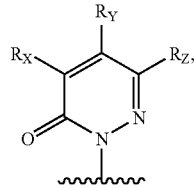

$R_X$ is thiophen-3-yl, $R_Y$ is tetrazol-2-yl, $R_Z$ is hydrogen, m=s=1, $R_5$ is t-butyl, and $R_6$ is vinyl;

Example 156

Compound of Formula I, wherein A is tBOC, B is H, G is OH, W is

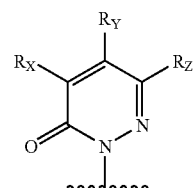

$R_X$ and $R_Y$ are each mercapto-2-pryrimidine, $R_Z$ is hydrogen, m=s=1, $R_5$ is t-butyl, and $R_6$ is vinyl;

Example 157

Compound of Formula I, wherein A is tBOC, B is H, G is OH, W is

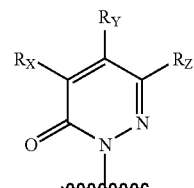

$R_X$ is bromo, $R_Y$ is mercapto-2-pryrimidine, $R_Z$ is hydrogen, m=s=1, $R_5$ is t-butyl, and $R_6$ is vinyl;

Example 158

Compound of Formula I, wherein A is tBOC, B is H, G is OH, W is

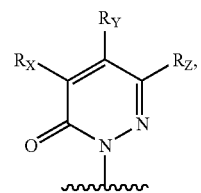

$R_X$ is thiophen-3-yl, $R_Y$ is mercapto-2-pyrimidine, $R_Z$ is hydrogen, m=s=1, $R_5$ is t-butyl, and $R_6$ is vinyl;

Example 159

Compound of Formula I, wherein A is tBOC, B is H, G is OH, W is

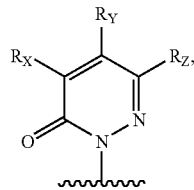

$R_X$ and $R_Y$ are each thiazol-2-yl, $R_Z$ is hydrogen, m=s=1, $R_5$ is t-butyl, and $R_6$ is vinyl;

Example 160

Compound of Formula I, wherein A is tBOC, B is H, G is OH, W is

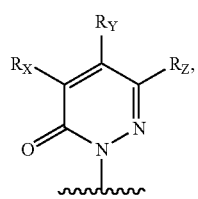

$R_X$ and $R_Y$ are each imidazol-1-yl, $R_Z$ is hydrogen, m=s=1, $R_5$ is t-butyl, and $R_6$ is vinyl;

Example 161

Compound of Formula I, wherein A is tBOC, B is H, G is OH, W is

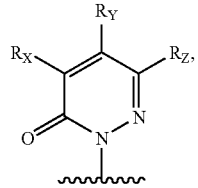

$R_X$ is 2-(cyclopropylamino)-thiazol-4-yl, $R_Y$ is 4-methoxyphenyl, $R_Z$ is hydrogen, m=s=1, $R_5$ is t-butyl, and $R_6$ is vinyl;

Example 162

Compound of Formula I, wherein A is tBOC, B is H, G is OH, W is

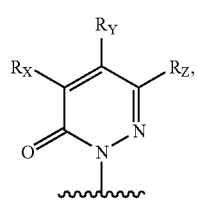

$R_X$ and $R_Y$ taken together are 6-methoxy-isoquinolinyl, $R_Z$ is hydrogen, m=s=1, $R_5$ is t-butyl, and $R_6$ is vinyl;

Example 163

Compound of Formula I, wherein A is —(C=O)—O—$R_1$, wherein $R_1$ is cyclopentyl, B is H, G is OH, W is

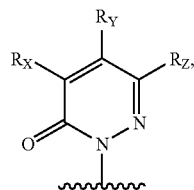

$R_X$ is thiophen-3-yl, $R_Y$ is thiophen-3-yl, $R_Z$ is hydrogen, m=s=1, $R_5$ is t-butyl, and $R_6$ is vinyl;

Example 164

Compound of Formula I, wherein A is —(C=O)—O—$R_1$, wherein $R_1$ is cyclobutyl, B is H, G is OH, W is

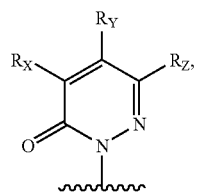

$R_X$ is thiophen-3-yl, $R_Y$ is thiophen-3-yl, $R_Z$ is hydrogen, m=s=1, $R_5$ is t-butyl, and $R_6$ is vinyl;

Example 165

Compound of Formula I, wherein A is —(C=O)—O—$R_1$, wherein $R_1$ is cyclohexyl, B is H, G is OH, W is

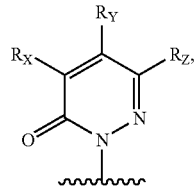

$R_X$ is thiophen-3-yl, $R_Y$ is thiophen-3-yl, $R_Z$ is hydrogen, m=s=1, $R_5$ is t-butyl, and $R_6$ is vinyl;

Example 166

Compound of Formula I, wherein A is —(C=O)—O—$R_1$, wherein $R_1$ is

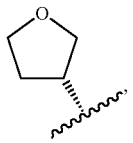

B is H, G is OH, W is

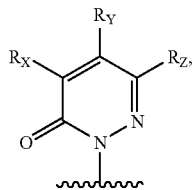

$R_X$ is thiophen-3-yl, $R_Y$ is thiophen-3-yl, $R_Z$ is hydrogen, $m=s=1$, $R_5$ is t-butyl, and $R_6$ is vinyl;

Example 167

Compound of Formula I, wherein A is —(C=O)—O—$R_1$, wherein $R_1$ is

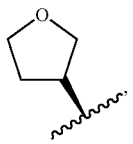

B is H, G is OH, W is

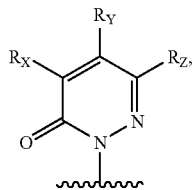

$R_X$ is thiophen-3-yl, $R_Y$ is thiophen-3-yl, $R_Z$ is hydrogen, $m=s=1$, $R_5$ is t-butyl, and $R_6$ is vinyl; and

Example 168

Compound of Formula I, wherein A is —(C=O)—O—$R_1$, wherein $R_1$ is

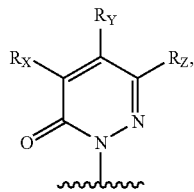

B is H, G is OH, W is

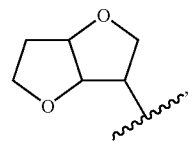

$R_X$ is thiophen-3-yl, $R_Y$ is thiophen-3-yl, $R_Z$ is hydrogen, $m=s=1$, $R_5$ is t-butyl, and $R_6$ is vinyl.

Although the invention has been described with respect to various preferred embodiments, it is not intended to be limited thereto, but rather those skilled in the art will recognize that variations and modifications may be made therein which are within the spirit of the invention and the scope of the appended claims.

---

What is claimed is:

1. A compound of formula (I)

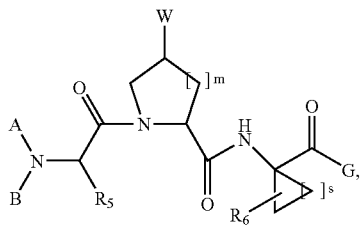

or pharmaceutically acceptable salt, ester, or prodrug thereof, wherein

A and B are independently selected from $R_1$, —C(O)$R_1$, —C(O)O$R_1$, —C(O)N$R_3R_4$, —C(S)N$R_3R_4$, or —S(O)$_n R_1$;

G is selected from —$R_1$, —O$R_1$, —C(O)$R_1$, —C(O)O$R_1$, —C(O)N$R_3R_4$, —N$R_3R_4$, or —N($R_3$)S(O)$_n R_1$;

W is selected from a substituted or unsubstituted heterocyclic, or a substituted or unsubstituted heteroaromatic;

Each $R_1$ is independently selected from: hydrogen, deuterium, acyl, silane, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group;

Each of $R_3$ and $R_4$ is independently selected from: hydrogen, acyl, ester, optionally substituted amino acyl, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, a substituted or unsubstituted heterocyclic group; or can be taken together with the nitrogen atom to which they are attached to form a substituted or unsubstituted heterocyclic or heteroaromatic ring;

Each of $R_5$ and $R_6$ are independently selected from: hydrogen, deuterium, acyl, silane, a substituted or unsubstituted, saturated or unsaturated aliphatic group, a substituted or unsubstituted, saturated or unsaturated alicyclic group, a substituted or unsubstituted aromatic group, a substituted or unsubstituted heteroaromatic group, or a substituted or unsubstituted heterocyclic group alkoxy, alkyl amine, hydroxy, hydroxyl amine, carboxy, ester, amine;

m is 0, 1, or 2;

n is 0, 1, or 2; and s is 1–6.

2. A compound of formula I, according to claim 1, wherein W is selected from substituted or unsubstituted tetrazolyl.

3. A compound of formula I, according to claim 1, wherein W is selected from substituted or unsubstituted triazolyl.

4. A compound of formula I, according to claim 1, selected from:

Compound of Formula I, wherein A is tBOC, B is H, G is OH, W is

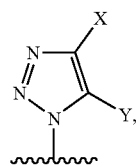

X is H, Y is 4-t-butylphenyl, m=s=1, $R_5$ is t-butyl, and $R_6$ is vinyl;

Compound of Formula I, wherein A is tBOC, B is H, G is OH, W is

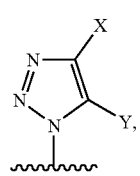

X is 4-t-butylphenyl, Y is H, m=s=1, $R_5$ is t-butyl, and $R_6$ is vinyl;

Compound of Formula I, wherein A is tBOC, B is H, G is OH, W is

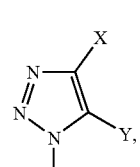

X and V are taken together is phenyl, m=s=1, $R_5$ is t-butyl, and $R_6$ is vinyl;

Compound of Formula I, wherein A is tBOC, B is H, G is OH, W is

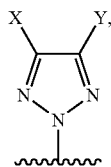

X and Y taken together is phenyl, m=s=1, R$_5$ is t-butyl, and R$_6$ is vinyl;

Compound of Formula I, wherein A is tBOC, B is H, G is OH, W is

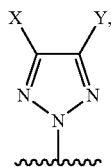

X is Y is phenyl, m=s=1, R$_5$ is t-butyl, and R$_6$ is vinyl;

Compound of Formula I, wherein A is tBOC, B is H, G is OEt, W is

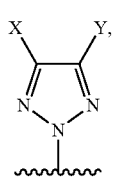

X is Y is phenyl, m=s=1, R$_5$ is t-butyl, and R$_6$ is vinyl;

Compound of Formula I, wherein A is tBOC, B is H, G is OH, W is

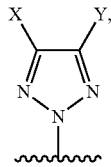

X is Y is phenyl, m=s=1, R$_5$ is t-butyl, and R$_6$ is vinyl;

Compound of Formula I, wherein A is tBOC, B is H, G is OH, W is

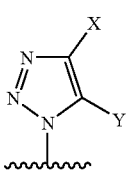

X is Y is phenyl, m=s=1, R$_5$ is t-butyl, and R$_6$ is vinyl;

Compound of Formula I, wherein A is tBOC, B is H, G is OH, W is

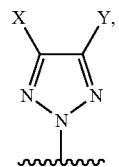

X is n-propyl, Y is phenyl, m=s=1, R$_5$ is t-butyl, and R$_6$ is vinyl;

Compound of Formula I wherein A is tBOC, B is H, G is OH, W is

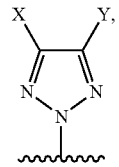

X is m-methoxyphenyl, Y is p-methoxyphenyl, m=s=1, R$_5$ is t-butyl, and R$_6$ is vinyl;

Compound of Formula I, wherein A is tBOC, B is H, G is OH, W is

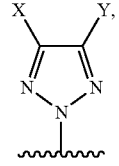

X is m-bromophenyl, Y is p-methoxyphenyl, m=s=1, R$_5$ is t-butyl, and R$_6$ is vinyl;

Compound of Formula I, wherein A is tBOC, B is H, G is OH, W is

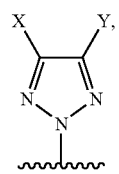

X is 1-napthyl, Y is p-methoxyphenyl, m=s=1, R$_5$ is t-butyl, and R$_6$ is vinyl;

Compound of Formula I, wherein A is tBOC, B is H, G is OH, W is

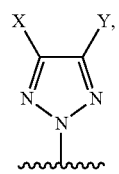

X is 2-thienyl, Y is p-methoxyphenyl, m=s=1, $R_5$ is t-butyl, and $R_6$ is vinyl;

Compound of Formula I, wherein A is tBOC, B is H, G is OH, W is

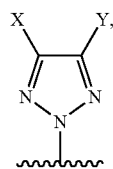

X is 3-thienyl, Y is p-methoxyphenyl, m=s=1, $R_5$ is t-butyl, and $R_6$ is vinyl;

Compound of Formula I, wherein A is tBOC, B is H, G is OH, W is

X is 4-pyrazolyl, Y is p-methoxyphenyl, m=s=1, $R_5$ is t-butyl, and $R_6$ is vinyl;

Compound of Formula I, wherein A is tBOC, B is H, G is OH, W is

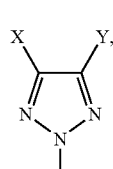

X is 3-pyridyl, Y is p-methoxyphenyl, m=s=1, $R_5$ is t-butyl, and $R_6$ is vinyl;

Compound of Formula I, wherein A is tBOC, B is H, G is OH, W is

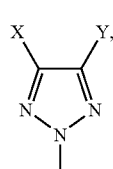

X is 2-pyridyl, Y is p-methoxyphenyl, m=s=1, $R_5$ is t-butyl, and $R_6$ is vinyl;

Compound of Formula I, wherein A is tBOC, B is H, G is OH, W is

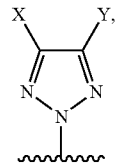

X is 2-thiazolyl, Y is p-methoxyphenyl, m=s=1, $R_5$ is t-butyl, and $R_6$ is vinyl;

Compound of Formula I, wherein A is tBOC, B is H, G is OH, W is

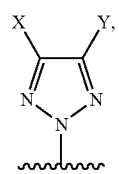

X is benzyl, Y is phenyl, m=s=1, $R_5$ is t-butyl, and $R_6$ is vinyl;

Compound of Formula I, wherein A is tBOC, B is H, G is OH, W is

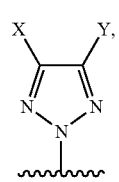

X is n-butyl, Y is phenyl, m=s=1, $R_5$ is t-butyl, and $R_6$ is vinyl;

Compound of Formula I, wherein A is tBOC, B is H, G is OH, W is

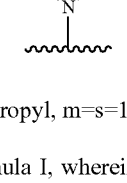

X is n-propyl, Y is n-propyl, m=s=1, $R_5$ is t-butyl, and $R_6$ is vinyl;

Compound of Formula I, wherein A is tBOC, B is H, G is OH, W is

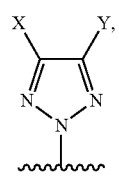

X is 4-(N,N-dimethylamino)phenyl, Y is phenyl, m=s=1, R₅ is t-butyl, and R₆ is vinyl;

Compound of Formula I, wherein A is tBOC, B is H, G is OH, W is

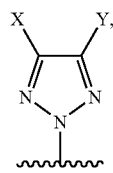

X is (N,N-diethylamino)methyl, Y is phenyl, m=s=1, R₅ is t-butyl, and R₆ is vinyl;

Compound of Formula I, wherein A is tBOC, A is H, G is OH, W is

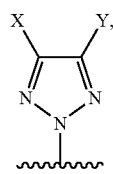

X is N,N-diethylaminocarbonyl, Y is phenyl, m=s=1, R₅ is t-butyl, and R₆ is vinyl;

Compound of Formula I, wherein A is tBOC, B is H, G is OH, W is

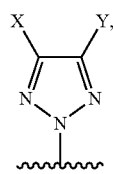

X is m-chlorophenyl, Y is 4-ethoxyphenyl, m=s=1, R₅ is t-butyl, and R₆ is vinyl;

Compound of Formula I, wherein A is tBOC, B is H, G is OH, W is

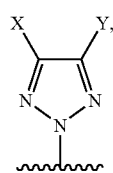

X is 2-phenylethenyl, Y is phenyl, m=s=1, R₅ is t-butyl, and R₆ is vinyl;

Compound of Formula I, wherein A is tBOC, B is H, G is OH, W is 5,6-methylbenzotriazole, m=s=1, R₅ is t-butyl, and R₆ is vinyl;

Compound of Formula I, wherein A is tBOC, B is H, G is OH, W is

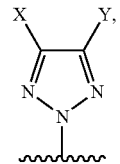

X is N-ethylaminocarbonyl, Y is phenyl, m=s=1, R₅ is t-butyl, and R₆ is vinyl;

Compound of Formula I, wherein A is —(C=O)—O—R₁, wherein R₁ is cyclopentyl, B is H, G is OH, W is

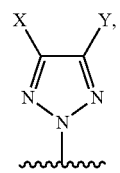

X is phenyl, Y is phenyl, m=s=1, R₅ is t-butyl, and R₆ is vinyl;

Compound of Formula I, wherein A is —(C=O)—O—R₁, wherein R₁ is cyclobutyl, B is H, G is OH, W is

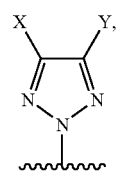

X is phenyl, Y is phenyl, m=s=1, R₅ is t-butyl, and R₆ is vinyl;

Compound of Formula I, wherein A is —(C=O)—O—R₁, wherein R₁ is cyclohexyl, B is H, G is OH, W is

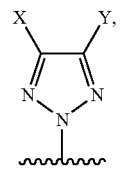

X is phenyl, Y is phenyl, m=s=1, R₅ is t-butyl, and R₆ is vinyl;

Compound of Formula I, wherein A is —(C=O)—O—R₁, wherein R₁ is

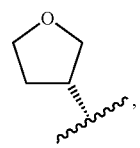

B is H, G is OH, W is

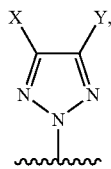

X is phenyl, Y is phenyl, m=s=1, R$_5$ is t-butyl, and R$_6$ is vinyl;

Compound of Formula I, wherein A is —(C=O)—O—R$_1$, wherein R$_1$ is

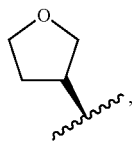

B is H, G is OH, W is

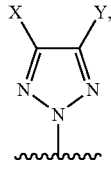

X is phenyl, V is phenyl, m=s=1, R$_5$ is t-butyl, and R$_6$ is vinyl;

Compound of Formula I, wherein A is —(C=O)—O—R$_1$, wherein R$_1$ is

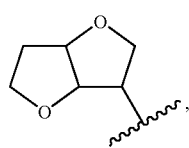

B is H, G is OH, W is

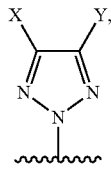

X is phenyl, Y is phenyl, m=s=1, R$_5$ is t-butyl, and R$_6$ is vinyl;

Compound of Formula I, wherein A is —(C=O)—R$_1$, wherein R$_1$ is cyclopentyl, B is H, G is OH, W is

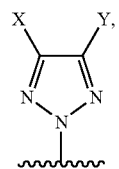

X is phenyl, Y is phenyl, m=s=1, R$_5$ is t-butyl, and R$_6$ is vinyl;

Compound of Formula I, wherein A is —(C=O)—NH—R$_1$, wherein R$_1$ is cyclopentyl, B is H, G is OH, W is

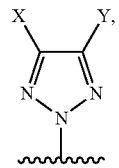

X is phenyl, Y is phenyl, m=s=1, R$_5$ is t-butyl, and R$_6$ is vinyl;

Compound of Formula I, wherein A is —(C=S)—NH—R$_1$, wherein R$_1$ is cyclopentyl, B is H, G is OH, W is

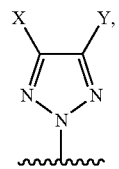

X is phenyl, Y is phenyl, m=s=1, R$_5$ is t-butyl, and R$_6$ is vinyl;

Compound of Formula I, wherein A is —S(O)$_2$—R$_1$, wherein R$_1$ is cyclopentyl, B is H, G is OH, W is

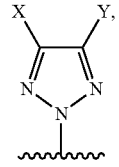

X is phenyl, Y is phenyl, m=s=1, R$_5$ is t-butyl, and R$_6$ is vinyl;

Compound of Formula I, wherein A is —(C=O)—O—R$_1$, R$_1$ is cyclopentyl, B is H, G is —O-phenethyl, W is

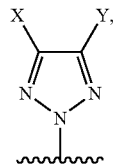

X is phenyl, Y is phenyl, m=s=1, R$_5$ is t-butyl, and R$_6$ is vinyl;

Compound of Formula I, wherein A is —(C=O)—O—R$_1$, R$_1$ is cyclopentyl, B is H, G is —NH-phenethyl, W is

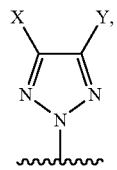

X is phenyl, Y is phenyl, m=s=1, R$_5$ is t-butyl, and R$_6$ is vinyl;

Compound of Formula I, wherein A is —(C=O)—O—R$_1$, R$_1$ is cyclopentyl, B is H, G is NHS(O)$_2$-phenethyl, W is

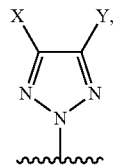

X is phenyl, Y is phenyl, m=s=1, R$_5$ is 1-butyl, and R$_6$ is vinyl;

Compound of Formula I, wherein A is —(C=O)—O—R$_1$, R$_1$ is cyclopentyl, B is H, G is —(C=O)—OH W is

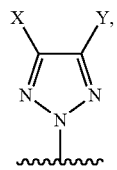

X is phenyl, Y is phenyl, m=s=1, R$_5$ is t-butyl, and R$_6$ is vinyl;

Compound of Formula I, wherein A is —(C$_0$)—O—R$_1$, R$_1$ is cyclopentyl, B is H, G is —(C=O)—O-phenethyl, W is

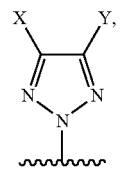

X is phenyl, Y is phenyl, m=s=1, R$_5$ is t-butyl, and R$_6$ is vinyl;

Compound of Formula I, wherein A is —(C=O)—O—R$_1$, R$_1$ is cyclopentyl, B is H, G is —(C=O)—NH-phenethyl, W is

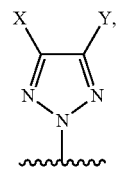

X is phenyl, Y is phenyl, m=s=1, R$_5$ is t-butyl, and R$_6$ is vinyl;

Compound of Formula I, wherein A is —(C=O)—O—R$_1$, R$_1$ is cyclopentyl, B is H, G is —(C=O)—NH—S(O)$_2$-benzyl, W is

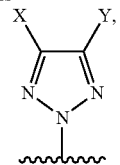

X is phenyl, Y is phenyl, m=s=1, R$_5$ is t-butyl, and R$_6$ is vinyl;

Compound of Formula I, wherein A is tBOC, B is H, G is OH, W is

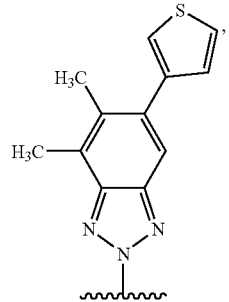

m=s=1, R$_5$ is t-butyl, end R$_6$ is vinyl;

Compound of Formula I, wherein A is tBOC, B is H, G is OH, W is

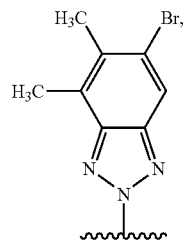

m=s=1, R$_5$ is t-butyl, and R$_6$ is vinyl; or

Compound of Formula I, wherein A is tBOC, B is H, G is OH, W is

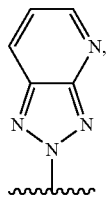

m=s=1, $R_5$ is t-butyl, and $R_6$ is vinyl;

Compound of Formula I, wherein A is tBOC, B is H, G is OH, W is

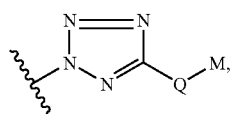

Q is absent, M is phenyl, m=s=1, $R_5$ is t-butyl, and $R_6$ is vinyl;

Compound of Formula I, wherein A is tBOC, B is H, G is OH, W is

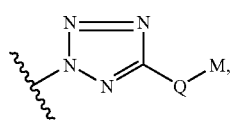

Q is absent, M is 2-bromophenyl, m=s=1, $R_5$ is t-butyl, and $R_6$ is vinyl;

Compound of Formula I, wherein A is tBOC, B is H, G is OH, W is

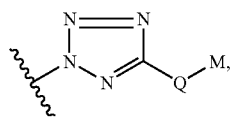

Q is absent, M is 3-bromophenyl, m=s=1, $R_5$ is t-butyl, and $R_6$ is vinyl;

Compound of Formula I, wherein A is tBOC, B is H, G is OH, W is

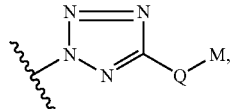

Q is absent, M is 4-bromophenyl, m=s=1, $R_5$ is t-butyl, and $R_6$ is vinyl;

Compound of Formula I, wherein A is tBOC, B is H, G is OH, W is

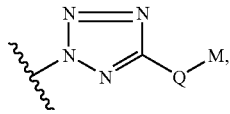

Q is absent, M is 5-Bromo-2-thienyl, m=s=1, $R_5$ is t-butyl, and $R_6$ is vinyl;

Compound of Formula I, wherein A is tBOC, B is H, G is OH, W is

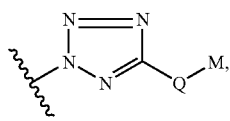

Q is absent, M is 2-bromo-4-pyridyl, m=s=1, $R_5$ is t-butyl, and $R_6$ is vinyl;

Compound of Formula I, wherein A is tBOC, B is H, G is OH, W is

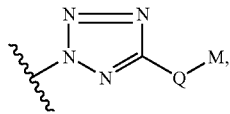

Q is absent, M is 2-biphenyl, m=s=1, $R_5$ is t-butyl, and $R_6$ is vinyl;

Compound of Formula I, wherein A is tBOC, B is H, G is OH, W is

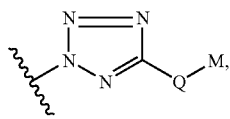

Q is absent M is 3-biphenyl, m=s=1, $R_5$ is t-butyl, and $R_6$ is vinyl;

Compound of Formula I, wherein A is tBOC, B is H, G is OH, W is

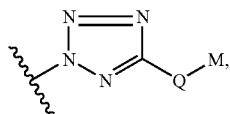

Q is absent, M is 4-biphenyl, m=s=1, $R_5$ is t-butyl, and $R_6$ is vinyl;

Compound of Formula I, wherein A is tBOC, B is H, G is OH, W is

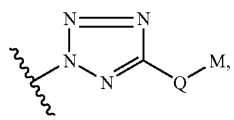

Q is absent, M is 3-(3-thienyl)phenyl, m=s=1, $R_5$ is t-butyl, and $R_6$ is vinyl;
  Compound of Formula I, wherein A is tBOC, B is H, G is OH, W is

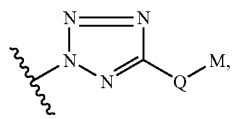

Q is absent, M is 3-(p-trifluoromethoxyphenyl)phenyl, m=s=1, $R_5$ is t-butyl, and $R_6$ is vinyl;
  Compound of Formula I, wherein A is tBOC, B is H, G is OH, W is

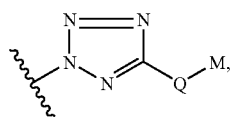

Q is absent, M is 3-(p-cyanophenyl)phenyl, m=s=1, $R_5$ is t-butyl, and $R_6$ is vinyl;
  Compound of Formula I, wherein A is tBOC, B is H, G is OH, W is

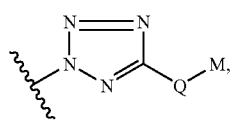

Q is absent, M is 4-(3-thienyl)phenyl, m=s=1, $R_5$ is t-butyl, and $R_6$ is vinyl;
  Compound of Formula I, wherein A is tBOC, B is H, G is OH, W is

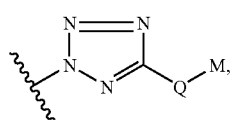

is absent, M is 4-(p-trifluoromethoxyphenyl)phenyl, m=s=1, $R_5$ is t-butyl, and $R_6$ is vinyl;
  Compound of Formula I, wherein A is tBOC, B is H, G is OH, W

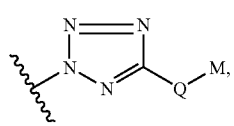

Q is absent, M is 4-(p-cyanophenyl)phenyl, m=s=1, $R_5$ is t-butyl, and $R_6$ is vinyl;
  Compound of Formula I, wherein A is tBOC, B is H, G is OH, W is

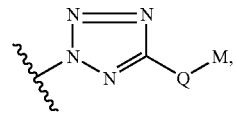

Q is absent, M is 5-phenyl-2-thienyl, m=s=1, $R_5$ is t-butyl, and $R_6$ is vinyl;
  Compound of Formula I, wherein A is tBOC, B is H, G is OH, W is

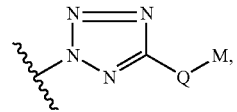

Q is absent, M is 5-phenyl-3-pyridyl, m=s=1, $R_5$ is t-butyl, and $R_6$ is vinyl;
  Compound of Formula I, wherein A is tBOC, B is H, G is OEt, W is

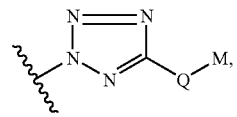

Q is absent, M is 3-chloro-4-hydroxyphenyl, m=s=1, $R_5$ is t-butyl, and $R_6$ is vinyl;
  Compound of Formula I, wherein A is tBOC, B is H, G is OH, W is

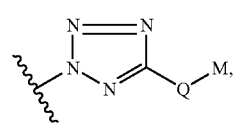

Q is absent, M is 3-chloro-4-hydroxyphenyl, m=s=1, $R_5$ is t-butyl, and $R_6$ is vinyl;
  Compound of Formula I, wherein A is tBOC, B is H, G is OH, W is

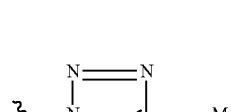

Q is absent, M is 3-bromo-4-hydroxyphenyl, m=s=1, $R_5$ is t-butyl, and $R_6$ is vinyl;
  Compound of Formula I, wherein A is tBOC, B is H, G is OH, W is

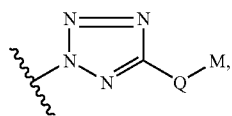

Q is absent, M is 2-methyl-4-bromophenyl, m=s=1, $R_5$ is t-butyl, and $R_6$ is vinyl;
  Compound of Formula I, wherein A is tBOC, B is H, G is OH, W is

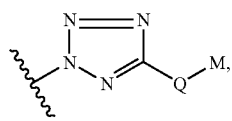

Q is absent, M is 3-methyl-4-bromophenyl, m=s=1, $R_5$ is t-butyl, and $R_6$ is vinyl;
  Compound of Formula I, wherein A is tBOC, B is H, G is OH, W is

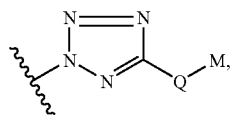

Q is absent M is n-propyl, m=s=1, $R_5$ is t-butyl, and $R_6$ is vinyl;
  Compound of Formula I, wherein A is tBOC, B is H, G is OH, W is

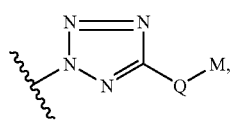

Q is absent M is n-butyl, m=s=1, $R_5$ is t-butyl, and $R_6$ is vinyl;
  Compound of Formula I, wherein A is tBOC, B is H, G is OH, W is

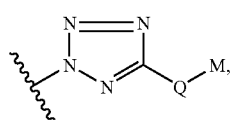

Q is absent, M is 4-ethoxyphenyl, m=s=1, $R_5$ is t-butyl, and $R_6$ is vinyl;
  Compound of Formula I, wherein A is tBOC, B is H, G is OH, W is

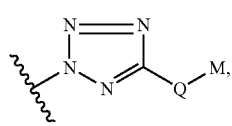

Q is absent, M is 4-propoxyphenyl, m=s=1, $R_5$ is t-butyl, and $R_6$ is vinyl;
  Compound of Formula I, wherein A is tBOC, B is H, G is OH, W is

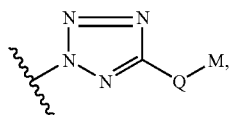

Q is absent, M is 4-butoxyphenyl, m=s=1, $R_5$ is t-butyl, and $R_6$ is vinyl;
  Compound of Formula I, wherein A is tBOC, B is H, G is OH, W is

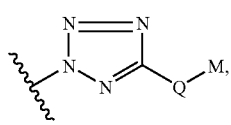

Q is absent, M is 3-methoxyphenyl, m=s=1, $R_5$ is t-butyl, end $R_6$ is vinyl;
  Compound of Formula I, wherein A is tBOC, B is H, G is OH, W is

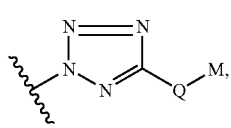

Q is absent, M is 3,4-dimethoxyphenyl, m=s=1, $R_5$ is t-butyl, and $R_6$ is vinyl;
  Compound of Formula I, wherein A is tBOC, B is H, G is OH, W is

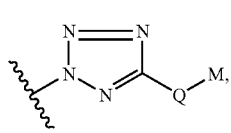

Q is absent, M is 4-methoxy-1-naphthyl, m=s=1, $R_5$ is t-butyl, and $R_6$ is vinyl;
  Compound of Formula I, wherein A is tBOC, B is H, G is OH, W is

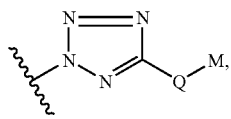

Q is absent, M is 4-phenoxyphenyl, m=s=1, $R_5$ is t-butyl, and $R_6$ is vinyl;

Compound of Formula I, wherein A is tBOC, B is H, G is OH, W is

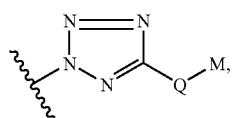

Q is absent, M is benzyl, m=s=1, $R_5$ is t-butyl, and $R_6$ is vinyl;

Compound of Formula I, wherein A is tBOC, B is H, G is OH, W is

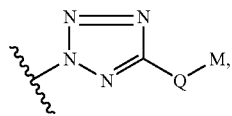

Q is absent M is p-phenylbenzyl, m=s=1, $R_5$ is t-butyl, and $R_6$ is vinyl;

Compound of Formula I, wherein A is tBOC, B is H, G is OH, W

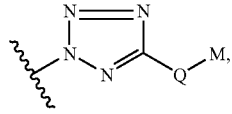

Q is absent, M is 3-chlorophenyl, m=s=1, $R_5$ is t-butyl, and $R_6$ is vinyl;

Compound of Formula I, wherein A is tBOC, B is H, G is OH, W is

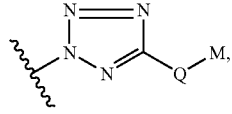

Q is absent, M is 3-fluorophenyl, m=s=1, $R_5$ is t-butyl, and $R_6$ is vinyl;

Compound of Formula I, wherein A is tBOC, B is H, G is OH, W is

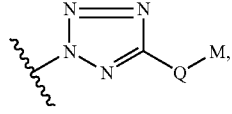

Q is absent, M is 3-methoxyphenyl, m=s=1, $R_5$ is t-butyl, and $R_6$ is vinyl;

Compound of Formula I, wherein A is tBOC, B is H, G is OH, W is

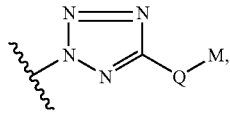

Q is absent, M is 3-phenoxyphenyl, m=s=1, $R_5$ is t-butyl, and $R_6$ is vinyl;

Compound of Formula I, wherein A is tBOC, B is H, G is OH, W is

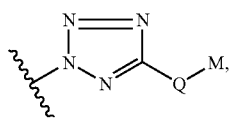

Q is absent, M is 3-benzyloxyphenyl, m=s=1, $R_5$ is t-butyl, and $R_6$ is vinyl;

Compound of Formula I, wherein A is tBOC, B is H, G is OH, W is

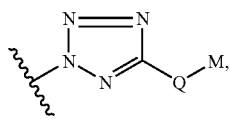

Q is absent, M is 3-trifluormethylphenyl, m=s=1, $R_5$ is t-butyl, and $R_6$ is vinyl;

Compound of Formula I, wherein A is tBOC, B is H, G is OH, W is

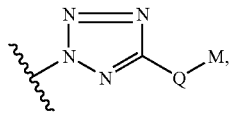

Q is absent M is 4-bromophenyl, m=s=1, $R_5$ is t-butyl, and $R_6$ is vinyl;

Compound of Formula I, wherein A is tBOC, B is H, G is OH, W is

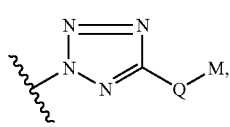

Q is absent, M is 4-fluorophenyl, m=s=1, $R_5$ is t-butyl, and $R_6$ is vinyl;

Compound of Formula I, wherein A is tBOC, B is H, G is OH, W is

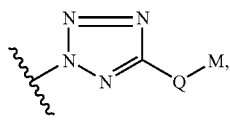

Q is absent, M is 4-methoxyphenyl, m=s=1, $R_5$ is t-butyl, and $R_6$ is vinyl;
  Compound of Formula I, wherein A is tBOC, B is H, G is OH, W is

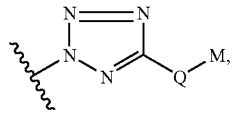

Q is absent, M is 4-ethoxyphenyl, m=s=1, $R_5$ is t-butyl, and $R_6$ is vinyl;
  Compound of Formula I, wherein A is tBOC, B is H, G is OH, W is

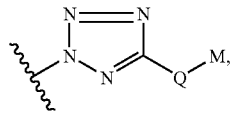

Q is absent, M is 4-trifluoromethylphenyl, m=s=1, $R_5$ is t-butyl, and $R_6$ is vinyl;
  Compound of Formula I, wherein A is tBOC, B is H, G is OH, W is

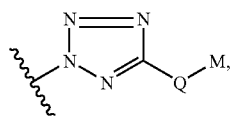

Q is absent, M is 3,5-di(trifluoromethyl)phenyl, m=s=1, $R_5$ is t-butyl, and $R_6$ is vinyl;
  Compound of Formula I, wherein A is tBOC, B is H, G is OH, W is

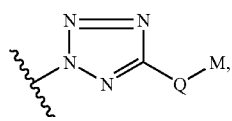

Q is absent, M is 4-(N,N-dimethylamino)-3,5-di(trifluoromethyl)phenyl, m=s=1, $R_5$ is t-butyl, and $R_6$ is vinyl;
  Compound of Formula I, wherein A is tBOC, B is H, G is OH, W is

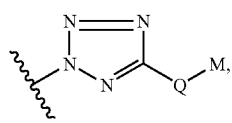

Q is absent, M is 2,4-dichlorophenyl, m=s=1, $R_5$ is t-butyl, and $R_6$ is vinyl;
  Compound of Formula I, wherein A is tBOC, B is H, G is OH, W is

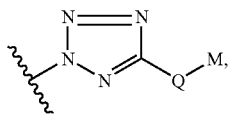

Q is absent, M is 3,5-dichlorophenyl, m=s=1, $R_5$ is t-butyl, and $R_6$ is vinyl;
  Compound of Formula I, wherein A is tBOC, B is H, G is OH, W is

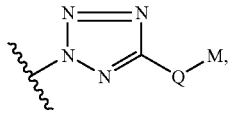

Q is absent, M is 3,4-dichlorophenyl, m=s=1, $R_5$ is t-butyl, and $R_6$ is vinyl;
  Compound of Formula I, wherein A is tBOC, B is H, G is OH, W is

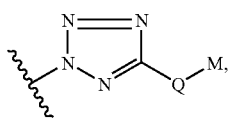

Q is absent, M is 2-pyridyl, m=s=1, $R_5$ is t-butyl, and $R_6$ is vinyl;
  Compound of Formula I, wherein A is tBOC, B is H, G is OH, W is

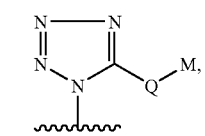

Q is absent, M is 2-pyridyl, m=s=1, $R_5$ is t-butyl, and $R_6$ is vinyl;
  Compound of Formula I, wherein A is tBOC, B is H, G is OH, W is

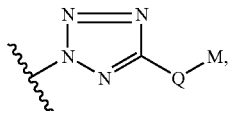

Q is absent, M is 3-pyridyl, m=s=1, $R_5$ is t-butyl, and $R_6$ is vinyl;
  Compound of Formula I, wherein A is tBOC, B is H, G is OH, W is

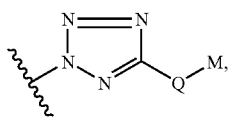

Q is absent, M is 4-pyridyl, m=s=1, $R_5$ is t-butyl, and $R_6$ is vinyl;

Compound of Formula I, wherein A is tBOC, B is H, G is OH, W is

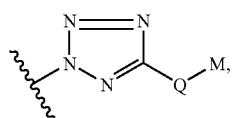

Q is absent, M is 4-methoxy-3-bromophenyl, m=s=1, $R_5$ is t-butyl, and $R_6$ is vinyl;

Compound of Formula I, wherein A is tBOC, B is H, G is OH, W is

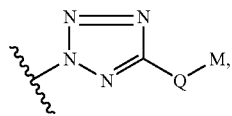

Q is absent, M is 4-(methylcyclopropane)phenyl, m=s=1, $R_5$ is t-butyl, and $R_6$ is vinyl;

Compound of Formula I, wherein A is tBOC, B is H, G is OH, W is

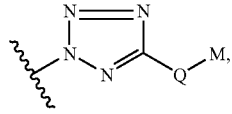

Q is absent, M is 3-chloro-4-(methylcyclopropane)phenyl, m=s=1, $R_5$ is t-butyl, and $R_6$ is vinyl;

Compound of Formula I, wherein A is tBOC, B is H, G is OH, W is

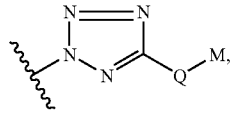

Q is absent, M is 3-chloro-4-methoxyphenyl, m=s=1, $R_5$ is t-butyl, and $R_6$ is vinyl;

Compound of Formula I, wherein A is tBOC, B is H, G is OH, W is

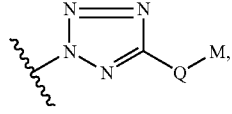

Q is absent, M is 3-chloro-4-ethoxyphenyl, m=s=1, $R_5$ is t-butyl, and $R_6$ is vinyl;

Compound of Formula I, wherein A is tBOC, B is H, G is OH, W is

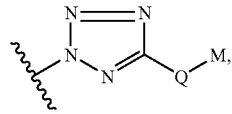

Q is absent, M is 3-bromo-4-ethoxyphenyl, m=s=1, $R_5$ is t-butyl, and $R_6$ is vinyl;

Compound of Formula I, wherein A is tBOC, B is H, G is OH, W is

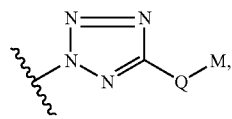

Q is absent, M is 3-chloro-4-(2-hydroxyethoxy)phenyl, m=s=1, $R_5$ is t-butyl, and $R_6$ is vinyl;

Compound of Formula I, wherein A is tBOC, B is H, G is OH, W is

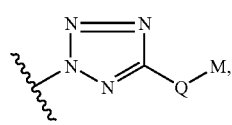

Q is absent, M is 3-bromo-4-(2-hydroxyethoxy)phenyl, m=s=1, $R_5$ is t-butyl, and $R_6$ is vinyl;

Compound of Formula I, wherein A is tBOC, B is H, G is OH, W is

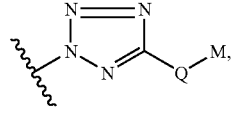

Q is absent, M is 3-chloro-4-(O-allyl)phenyl, m=s=1, $R_5$ is t-butyl, and $R_6$ is vinyl;

Compound of Formula I, wherein A is tBOC, B is H, G is OH, W is

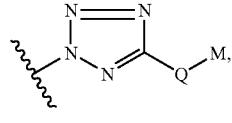

Q is absent, M is 3-bromo-4-(O-allyl)phenyl, m=s=1, $R_5$ is t-butyl, and $R_6$ is vinyl;

Compound of Formula I, wherein A is tBOC, B is H, G is OH, W is

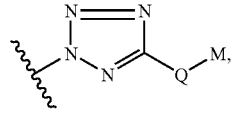

Q is absent, M is 3-chloro-4-(O—CH$_2$SCH$_3$)phenyl, m=s=1, R$_5$ is t-butyl, and R$_6$ is vinyl;
  Compound of Formula I, wherein A is tBOC, B is H, G is OH, W is

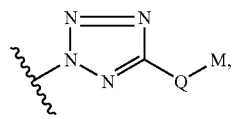

Q is absent, M is 3-chloro-4-(O—CH$_2$SCH$_3$)phenyl, m=s=1, R$_5$ is t-butyl, and R$_6$ is vinyl;
  Compound of Formula I, wherein A is tBOC, B is H, G is OH, W is

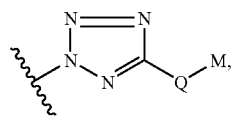

wherein Q is —CH$_2$—, M is

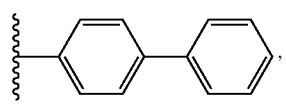

m=s=1, R$_5$ is t-butyl, and R$_6$ is vinyl;
  Compound of Formula I, wherein A is tBOC, B is H, G is OH, W is

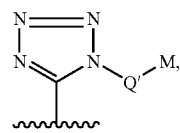

wherein Q' is —CH$_2$—, M is

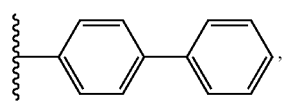

m=s=1, R$_5$ is t-butyl, and R$_6$ is vinyl;
  Compound of Formula I, wherein A is —(C=O)—O—R$_1$, wherein R$_1$ is cyclopentyl, B is H, G is OH, W is

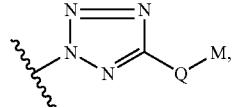

Q is absent, M is phenyl, m=s=1, R$_5$ is t-butyl, and R$_6$ is vinyl;

Compound of Formula I, wherein A is —(C=O)—O—R$_1$, wherein R$_1$ is cyclobutyl, B is H, G is OH, W is

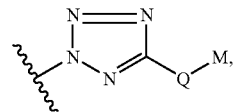

Q is absent, M is phenyl, m=s=1, R$_5$ is t-butyl, and R$_6$ is vinyl;
  Compound of Formula I, wherein A is —(C=O)—O—R$_1$, wherein R$_1$ is cyclohexyl, B is H, G is OH, W is

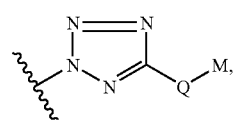

Q is absent, M is phenyl, m=s=1, R$_5$ is t-butyl, and R$_6$ is vinyl;
  Compound of Formula I, wherein A is —(C=O)—O—R$_1$, wherein R$_1$ is

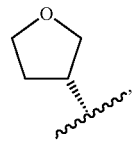

B is H, G is OH, W is

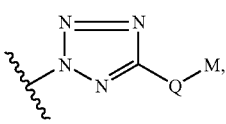

Q is absent M is phenyl, m=s=1, R$_5$ is t-butyl, and R$_6$ is vinyl;
  Compound of Formula I, wherein A is —(C=O)—O—R$_1$, wherein R$_1$ is

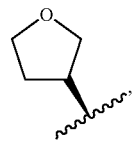

B is H, G is OH, W is

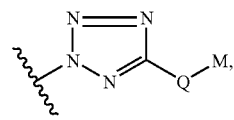

Q is absent, M is phenyl, m=s=1, R$_5$ is t-butyl, and R$_6$ is vinyl;

Compound of Formula I, wherein A is —(C=O)—O—R₁, wherein R₁ is

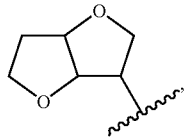

B is H, G is OH, W is

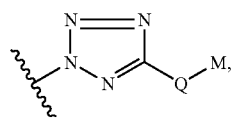

Q is absent, M is phenyl, m=s=1, R₅ is t-butyl, and R₆ is vinyl;

Compound of Formula I, wherein A is —(C=O)—R₁, wherein R₁ is cyclopentyl, B is H, G is OH, W is

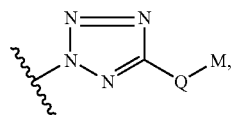

Q is absent M is phenyl, m=s=1, R₅ is t-butyl, and R₆ is vinyl;

Compound of Formula I, wherein A is —(C=O)—NH—R₁, wherein R₁ is cyclopentyl B is H, G is OH, W is

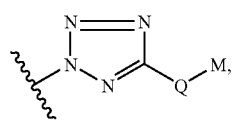

Q is absent M is phenyl, m=s=1, R₅ is t-butyl, and R₆ is vinyl;

Compound of Formula I, wherein A is —(C=S)—NH—R₁, wherein R₁ is cyclopentyl, B is H, G is OH, W is

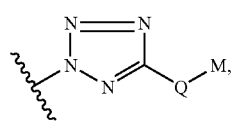

Q is absent M is phenyl, m=s=1, R₅ is t-butyl, and R₆ is vinyl;

Compound of Formula I, wherein A is —S(O)₂—R₁, wherein R₁ is cyclopentyl, B is H, G is OH, W is

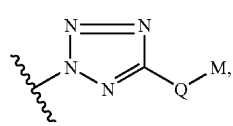

Q is absent, M is phenyl, m=s=1, R₅ is t-butyl, and R₆ is vinyl;

Compound of Formula I, wherein A is tBOC, B is H, G is —O—CH₂-cyclopentyl, W is

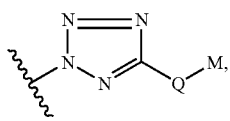

Q is absent, M is phenyl, m=s=1, R₅ is t-butyl, and R₆ is vinyl;

Compound of Formula I, wherein A is tBOC, B is H, G is —NHS(O)₂—CH₂-cyclopentyl, W is

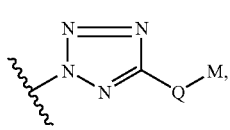

Q is absent, M is phenyl, m=s=1, R₅ is t-butyl, and R₆ is vinyl;

Compound of Formula I, wherein A is tBOC, B is H, G is —(C=O)—CH₂-cyclopentyl, W is

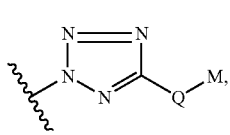

Q is absent M is phenyl, m=s=1, R₅ is t-butyl, and R₆ is vinyl;

Compound of Formula I, wherein A is tBOC, B is H, G is —(C=O)—O—CH₂-cyclopentyl, W is

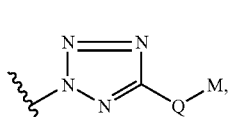

Q is absent, M is phenyl, m=s=1, R₅ is t-butyl, and R₆ is vinyl;

Compound of Formula I, wherein A is tBOC, B is H, G is —(C=O)—OH, W is

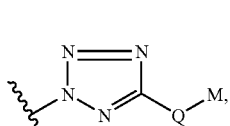

Q is absent, M is phenyl, m=s=1, R₅ s t-butyl, and R₆ is vinyl;

101

Compound of Formula I, wherein A is tBOC, B is H, G is —(C=O)—NH—CH$_2$-cyclopentyl, W is

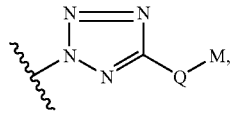

Q is absent, M is phenyl, m=s=1, R$_5$ is t-butyl, and R$_6$ is vinyl;

Compound of Formula I, wherein A is tBOC, B is H, Oet, W is

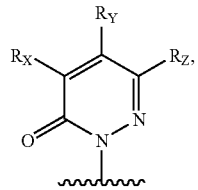

R$_x$ is bromo, R$_y$ is bromo, R$_z$ is hydrogen, m=s=1, R$_5$ is t-butyl, and R$_6$ is vinyl;

Compound of Formula I, wherein A is tBOC, B is H, G is Oet, W is

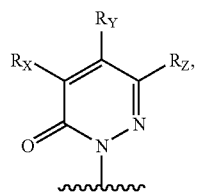

R$_x$ is thiophene=3-yl, R$_y$ is thiophene-3-yl, R$_z$ is hydrogen, m=s=1, R$_5$ is t-butyl, and R$_6$ is vinyl;

Compound of Formula I, wherein A is tBOC, B is H, G is OH, W is

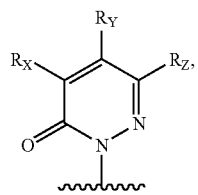

R$_x$ is thiophene=3-yl, R$_y$ is thiophene-3-yl, R$_z$ is hydrogen, m=s=1, R$_5$ is t-butyl, and R$_6$ is vinyl;

102

Compound of Formula I, wherein A is tBOC, B is H, G is OH W is

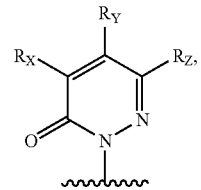

R$_x$ is phenyl, R$_y$ is phenyl, R$_z$ is hydrogen, m=s=1, R$_5$ is t-butyl, and R$_6$ is vinyl;

Compound of Formula I, wherein A is tBOC, B is H, G is OH, W is

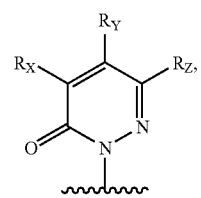

R$_x$ is 4-(trifluoromethoxy)phenyl R$_y$ is 4-(trifluoromethoxy)phenyl R$_z$ is hydrogen, m=s=1, R$_5$ is t-butyl, and R$_6$ is vinyl;

Compound of Formula I, wherein A is tBOC, B is H, G is OH, W is

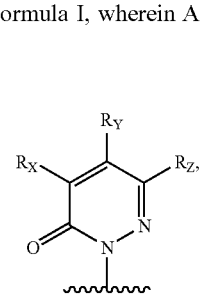

R$_x$ is 4-(methanesulfonyl)phenyl, R$_y$ is 4-(methanesulfonyl)phenyl, R$_z$ is hydrogen, m==1, R$_5$ is t-butyl, and R$_6$ is vinyl;

Compound of Formula I, wherein A is tBOC, B is H, G is OH, W is

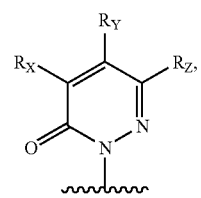

R$_x$ and R$_y$ are each 4-(cyano)phenyl, R$_z$ is hydrogen, m=s=1, R$_5$ is t-butyl, and R$_6$ is vinyl;

Compound of Formula I, wherein A is tBOC, B is H, G is OH, W is

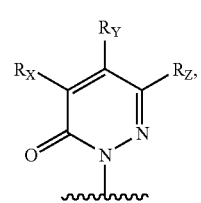

$R_x$ and $R_y$ are each 3-pyridyl, $R_z$ is hydrogen, m=s=1, $R_5$ is 4-butyl, and $R_6$ is vinyl;

Compound of Formula I, wherein A is tBOC, B is H, G is OH, W is

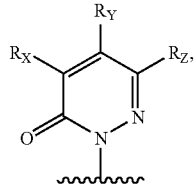

$R_x$ and $R_y$ are each 4-(morpholin-4-yl-methanonyl)phenyl, $R_z$ is hydrogen, m=s=1, $R_5$ is t-butyl, and $R_6$ is vinyl;

Compound of Formula I, wherein A is tBOC, B is H, G is OH, W is

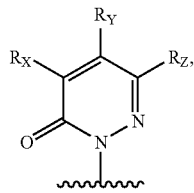

$R_x$ and $R_y$ are each bromo, $R_z$ is hydrogen, m=s=1, $R_5$ is t-butyl, and $R_6$ is vinyl;

Compound of Formula I, wherein A is tBOC, B is H, G is OH, W is

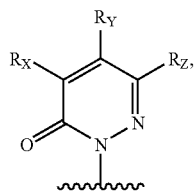

$R_x$ and $R_y$ taken together is phenyl, $R_z$ is 4-methoxyphenyl, m=s=1, $R_5$ is t-butyl, and $R_6$ is vinyl;

Compound of Formula I, wherein A is tBOC, B is H, G is OH, W is

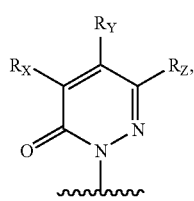

$R_x$ and $R_y$ taken together is phenyl, $R_z$ is 4-chlorophenyl, m=s=1, $R_5$ is t-butyl, and $R_6$ is vinyl;

Compound of Formula I, wherein A is tBOC, B is H, G is OH, W is

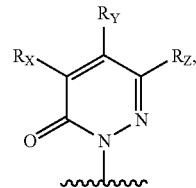

$R_x$ is 4-fluorophenyl, $R_y$ is hydrogen, $R_z$ is phenyl, m=s=1, $R_5$ is t-butyl, and $R_6$ is vinyl;

Compound of Formula I, wherein A is tBOC, B is H, G is OH, W is

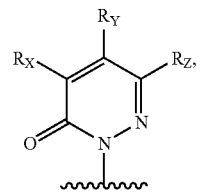

Rx is hydrogen, $R_y$ is 1-piperidyl, $R_z$ is phenyl, m=s=1, $R_5$ is t-butyl, and $R_6$ is vinyl;

Compound of Formula I, wherein A is tBOC, B is H, G is OEt, W is

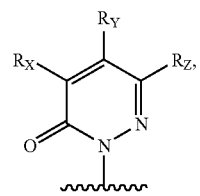

$R_x$ is hydrogen, $R_y$ is bromo, $R_z$ is phenyl, m=s=1, $R_5$ is t-butyl, and $R_6$ is vinyl;

Compound of Formula I, wherein A is tBOC, B is H, G is OH, W is

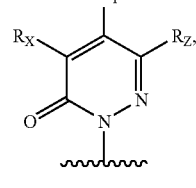

$R_x$ is hydrogen, $R_y$ is thiophen-3-yl, Rz is phenyl, m=s=1, $R_5$ is t-butyl, and $R_6$ is vinyl;

Compound of Formula I, wherein A is tBOC, B is H, G is OEt, W is

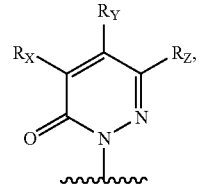

$R_x$ is bromo, $R_y$ is pyrrolid-1-yl, $R_z$ is hydrogen, m=s=1, $R_5$ is t-butyl, and $R_6$ is vinyl;

Compound of Formula I, wherein A is tBOC, B is H, G is OH, W is

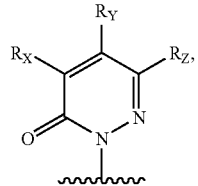

$R_x$ is thiophen-3-yl, $R_y$ is pyrrolid-1-yl, $R_z$ is hydrogen, m=s=1, $R_5$ is t-butyl, and $R_6$ is vinyl;

Compound of Formula I, wherein A is tBOC, B is H, G is OEt, W is

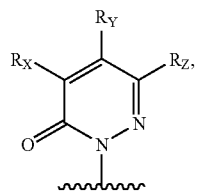

$R_x$ is bromo, $R_y$ is azido, $R_z$ is hydrogen, m=s=1, $R_5$ is t-butyl, and $R_6$ is vinyl;

Compound of Formula I, wherein A is tBOC, B is H, G is OEt, W is

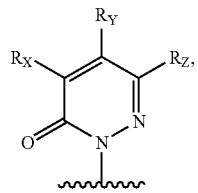

$R_x$ is thiophen-3-yl, $R_y$ is azido, $R_z$ is hydrogen, m=s=1, $R_5$ is t-butyl, and $R_6$ is vinyl;

Compound of Formula I, wherein A is tBOC, B is H, G is OH, W is

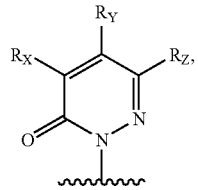

$R_x$ is thiophen-3-yl, $R_y$ is azido, $R_z$ is hydrogen, m=s=1, $R_5$ is t-butyl, and $R_6$ is vinyl;

Compound of Formula I, wherein A is tBOC, B is H, G is OH, W is

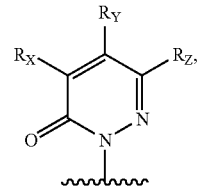

$R_x$ is thiophen-3-yl, $R_y$ is tetrazol-2-yl, $R_z$ is hydrogen, m=s=1, $R_5$ is t-butyl, and $R_6$ is vinyl;

Compound of Formula I, wherein A is tBOC, B is H, G is OH, W is

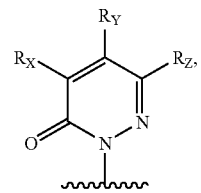

$R_1$ and $R_y$ are each mercapto-2-pryrimidine, $R_z$ is hydrogen, m=s=1, $R_5$ is t-butyl, and $R_6$ is vinyl;

Compound of Formula I, wherein A is tBOC, B is H, G is OH, W is

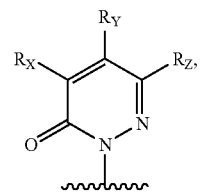

$R_x$ is bromo, $R_y$ is mercapto-2-pryrimidine, $R_z$ is hydrogen, m=s=1, $R_5$ is t-butyl, and $R_6$ is vinyl;

Compound of Formula I, wherein A is tBOC, B is H, G is OH, W is

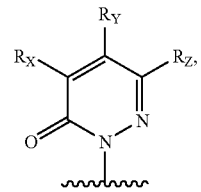

$R_x$ is thiophen-3-yl, $R_x$ is mercapto-2-pyrimidine, $R_z$ is hydrogen, m=s=1, $R_5$ is t-butyl, and $R_6$ is vinyl;

Compound of Formula I, wherein A is tBOC, B is H, G is OH, W is

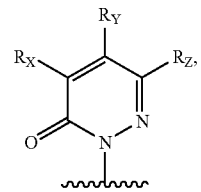

$R_x$ and $R_y$ are each thiazol-2-yl, $R_z$ is hydrogen, m=s=1, $R_5$ is t-butyl, and $R_6$ is vinyl;

Compound of Formula I, wherein A is tBOC, B is H, G is OH, W is

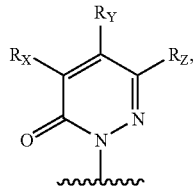

$R_x$ and $R_y$ are each imidazol-1-yl, $R_z$ is hydrogen, m=s=1, $R_5$ is t-butyl, and $R_6$ is vinyl;

Compound of Formula I, wherein A is tBOC, B is H, G is OH, W is

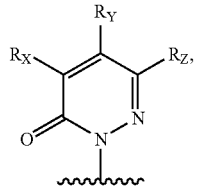

$R_x$ is 2-(cyclopropylamino)-thiazol-4-yl, $R_y$ is 4-methoxyphenyl, $R_z$ is hydrogen, m=s=1, $R_5$ is t-butyl, and $R_6$ is vinyl;

Compound of Formula I, wherein A is tBOC, B is H, G is OH, W is

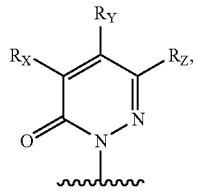

$R_x$ and $R_y$ taken together are 6-methoxy-isoquinolinyl, $R_z$ is hydrogen, m=s=1, $R_5$ is t-butyl, and $R_6$ is vinyl;

Compound of Formula I, wherein A is —(C=O)—O—$R_1$, wherein $R_1$ is cyclopentyl, B is H, G is OH, W is

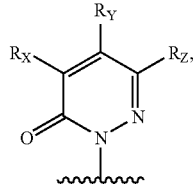

$R_x$ is thiophen-3-yl, $R_y$ is thiophen-3-yl, $R_z$ is hydrogen, m=s=1, $R_5$ is t-butyl, and $R_6$ is vinyl;

Compound of Formula I, wherein A is —(C=O)—O—$R_1$, wherein $R_1$ is cyclobutyl, B is H, G is OH, W is

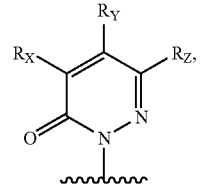

$R_x$ is thiophen-3-yl, Ry is thiophen-3-yl, $R_z$ is hydrogen, m=s=1, $R_5$ is t-butyl, and $R_6$ is vinyl;

Compound of Formula I, wherein A is —(C=O)—O—$R_1$, wherein $R_1$ is cyclohexyl, B is H, G is OH, W is

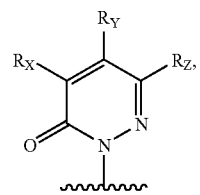

$R_x$ is thiophen-3-yl, $R_y$ is thiophen-3-yl, $R_z$ is hydrogen, m=s=1, $R_5$ is t-butyl, and $R_6$ is vinyl;

Compound of Formula I, wherein A is —(C=O)—O—$R_1$, wherein $R_1$ is

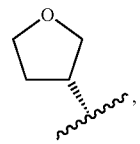

B is H, G is OH, W is

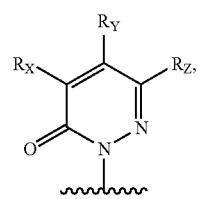

$R_x$ is thiophen-3-yl, $R_y$ is thiophen-3-yl, $R_z$ is hydrogen, m=s=1, $R_5$ is t-butyl, and $R_6$ is vinyl;

Compound of Formula I, wherein A is —(C=O)—O—$R_1$, wherein $R_1$ is

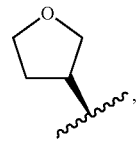

B is H, G is OH, W is

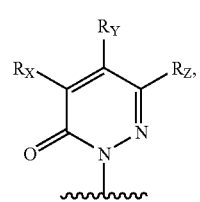

$R_x$ is thiophen-3-yl, $R_y$ is thiophen-3-yl, Rz is hydrogen, m=s=1, $R_5$ is t-butyl, and $R_6$ is vinyl; or Compound of Formula I, wherein A is —(C═O)—O—$R_1$, wherein $R_1$ is

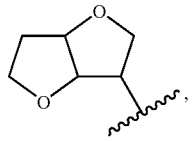

B is H, G is OH, W is

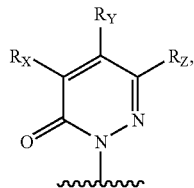

$R_x$ is thiophen-3-yl, $R_y$ is thiophen-3-yl, $R_z$ is hydrogen, m=s=1, $R_5$ is t-butyl, and $R_6$ is vinyl.

5. A pharmaceutical composition comprising a therapeutically effective amount of a compound according to claim 1, or a pharmaceutically acceptable salt, ester, or prodrug thereof, in combination with a pharmaceutically acceptable carrier or excipient.

6. A method of inhibiting the replication of hepatitis C virus, the method comprising contacting a hepatitis C viral NS3 protease with an amount of a compound according to claim 1.

7. A method of treating a hepatitis C viral infection in a subject, comprising administering to the subject a therapeutically effective amount of a pharmaceutical composition according to claim 5.

8. The method of claim 7 further comprising administering an additional anti-hepatitis C virus agent.

9. The method of claim 8, wherein said additional anti-hepatitis C virus agent is selected from the group consisting of: α-interferon, β-interferon, ribavarin, and adamantine.

10. The method of claim 8, wherein said additional and-hepatitis C virus agent is an inhibitor of other targets in the hepatitis C virus life cycle which is selected from the group consisting of: helicase, polymerase, metalloprotease, and IRES.

11. A compound of formula I, according to claim 1, wherein A is tBOC, —(C═O)—O—$R_1$, —(C═O)—$R_1$, —(C═O)—NH—$R_1$, —(C═S)—NH—$R_1$, or —S(O)$_2$—$R_1$.

12. A compound according to claim 11, wherein $R_1$ is cyclohexyl, cyclopentyl, cyclobutyl, tetrahydrofuran, or hexahydro-furo[3,2-b]furyl.

13. A compound of formula I, according to claim 1, wherein B is H.

14. A compound of formula I, according to claim 1, wherein $R_5$ is t-butyl.

15. A compound of formula I, according to claim 1, wherein $R_6$ is vinyl.

16. A compound of formula I, according to claim 1, wherein m is 1.

17. A compound of formula I, according to claim 1, wherein s is 1.

18. A compound according to claim 12, wherein B is H, $R_5$ is t-butyl, $R_6$ is vinyl, m is 1 and s is 1.

* * * * *